(12) United States Patent
Shuttleworth et al.

(10) Patent No.: US 10,407,435 B2
(45) Date of Patent: Sep. 10, 2019

(54) DIHETEROARYL HISTONE DEACETYLASE INHIBITORS AND THEIR USE IN THERAPY

(71) Applicant: Karus Therapeutics Limited, Oxfordshire (GB)

(72) Inventors: Stephen Joseph Shuttleworth, Oxfordshire (GB); Alexander Richard Liam Cecil, Oxfordshire (GB); Somhairle MacCormick, Oxfordshire (GB); William John Nodes, Oxfordshire (GB); Cyrille Davy Tomassi, Oxfordshire (GB)

(73) Assignee: Karus Therapeutics Limited, Oxfordshire (GB)

(*) Notice: Subject to any disclaimer, the term of this patent is extended or adjusted under 35 U.S.C. 154(b) by 0 days.

(21) Appl. No.: 15/522,188

(22) PCT Filed: Oct. 29, 2015

(86) PCT No.: PCT/GB2015/053260
§ 371 (c)(1),
(2) Date: Apr. 26, 2017

(87) PCT Pub. No.: WO2016/067040
PCT Pub. Date: May 6, 2016

(65) Prior Publication Data
US 2017/0313712 A1    Nov. 2, 2017

(30) Foreign Application Priority Data
Oct. 29, 2014    (GB) .................................. 1419228.0

(51) Int. Cl.

| A61K 31/497 | (2006.01) |
|---|---|
| C07D 491/048 | (2006.01) |
| C07D 403/12 | (2006.01) |
| C07D 413/12 | (2006.01) |
| C07D 241/20 | (2006.01) |
| C07D 417/12 | (2006.01) |
| C07D 487/04 | (2006.01) |
| A61K 31/4985 | (2006.01) |
| A61K 31/501 | (2006.01) |
| A61K 31/5025 | (2006.01) |
| A61K 31/506 | (2006.01) |
| A61K 31/519 | (2006.01) |
| A61K 31/5377 | (2006.01) |
| A61K 45/06 | (2006.01) |
| C07D 413/14 | (2006.01) |
| C07D 417/14 | (2006.01) |

(52) U.S. Cl.
CPC ........ *C07D 491/048* (2013.01); *A61K 31/497* (2013.01); *A61K 31/4985* (2013.01); *A61K 31/501* (2013.01); *A61K 31/506* (2013.01); *A61K 31/5025* (2013.01); *A61K 31/519* (2013.01); *A61K 31/5377* (2013.01); *A61K 45/06* (2013.01); *C07D 241/20* (2013.01); *C07D 403/12* (2013.01); *C07D 413/12* (2013.01); *C07D 413/14* (2013.01); *C07D 417/12* (2013.01); *C07D 417/14* (2013.01); *C07D 487/04* (2013.01)

(58) Field of Classification Search
CPC .............. A61K 31/497; A61K 31/4985; A61K 31/501; A61K 31/5025; A61K 31/506; A61K 31/519; A61K 31/5377; C07D 403/12; C07D 413/14; C07D 417/12; C07D 417/14; C07D 487/04; C07D 491/04
USPC ...... 514/235.8, 248, 252.01, 252.11, 255.05, 514/256, 275; 544/122, 236, 238, 253, 544/262, 280, 281, 295, 328, 331, 350, 544/357
See application file for complete search history.

(56) References Cited

U.S. PATENT DOCUMENTS

| 4,017,500 A | 4/1977 | Mayer et al. |
|---|---|---|
| 7,022,840 B2 | 4/2006 | Kobuke et al. |
| 8,748,458 B2* | 6/2014 | Shuttleworth ....... C07D 213/24 514/312 |
| 9,200,007 B2 | 12/2015 | Shuttleworth et al. |

(Continued)

FOREIGN PATENT DOCUMENTS

| CN | 101228161 A | 7/2008 |
|---|---|---|
| CN | 101663276 A | 3/2010 |

(Continued)

OTHER PUBLICATIONS

Alvarez-Rua C et al., 'Multiple Hydrogen Bonds and Tautomerism in Naphthyridine Derivatives,' New J Chem, May 7, 2004 (May 7, 2004)(ePub), 28:700-7.
Anonymous, 'Abstract No. 2009:1018972 CAPLUS,' for 'Lett Drug Des Disc, (2009), 6(4):268-77,' STN CA Caesar Accession No. 1028, Nov. 17, 2015 (Nov. 17, 2015), CAplus Chemical Abstract Service, American Chemical Society, Columbus, OH (Publ), pp. 1-2 XP-002751577.

(Continued)

*Primary Examiner* — Jeffrey H Murray
(74) *Attorney, Agent, or Firm* — Goodwin Procter LLP

(57) ABSTRACT

The present invention is a compound having the following formula: (Formula (I)) or a pharmaceutically acceptable salt thereof, wherein e.g. X is C or N; n is 1 to 10; each L is independently a 5- to 12-membered heteroaryl containing at least two nitrogen atoms; and W is a zinc-binding group. The compounds are useful as histone deacetylase (HDAC) inhibitors.

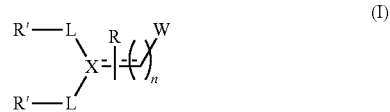

(I)

19 Claims, No Drawings

(56) References Cited

U.S. PATENT DOCUMENTS

| | | | |
|---|---|---|---|
| 9,266,879 B2 | 2/2016 | Shuttleworth et al. | |
| 9,340,503 B2* | 5/2016 | Shuttleworth | C07D 213/24 |
| 9,676,765 B2* | 6/2017 | Shuttleworth | A61K 45/06 |
| 9,862,685 B2 | 1/2018 | Shuttleworth et al. | |
| 10,150,763 B2 | 12/2018 | Shuttleworth et al. | |
| 2002/0099210 A1 | 7/2002 | Alexander et al. | |
| 2002/0151544 A1 | 10/2002 | Hayakawa et al. | |
| 2004/0106787 A1 | 6/2004 | Kobuke et al. | |
| 2004/0235888 A1 | 11/2004 | Yamamori et al. | |
| 2006/0239909 A1 | 10/2006 | Anderson et al. | |
| 2007/0135466 A1 | 6/2007 | Ledeboer et al. | |
| 2008/0125440 A1 | 5/2008 | Cai et al. | |
| 2008/0207729 A1 | 8/2008 | Pisano et al. | |
| 2008/0221112 A1 | 9/2008 | Yamamori et al. | |
| 2011/0201608 A1 | 8/2011 | Hoffmann et al. | |
| 2011/0305729 A1 | 12/2011 | Shuttleworth et al. | |
| 2012/0171199 A1 | 7/2012 | Dotson et al. | |
| 2012/0178737 A1 | 7/2012 | Shuttleworth et al. | |
| 2013/0109688 A1 | 5/2013 | Shuttleworth et al. | |
| 2014/0235671 A1 | 8/2014 | Shuttleworth et al. | |
| 2014/0378385 A1 | 12/2014 | Raje et al. | |
| 2015/0080395 A1 | 3/2015 | Shuttleworth et al. | |
| 2015/0361074 A1 | 12/2015 | Shuttleworth et al. | |
| 2016/0096804 A1 | 4/2016 | Shuttleworth et al. | |
| 2016/0108057 A1 | 4/2016 | Shuttleworth et al. | |
| 2017/0313698 A1 | 11/2017 | Shuttleworth et al. | |
| 2018/0086750 A1 | 3/2018 | Shuttleworth et al. | |
| 2018/0170876 A1 | 6/2018 | Shuttleworth et al. | |

FOREIGN PATENT DOCUMENTS

| | | | |
|---|---|---|---|
| CN | 104125946 A | 10/2014 | |
| EP | 0226099 A2 | 6/1987 | |
| EP | 0509400 A1 | 10/1992 | |
| EP | 0556396 A1 | 8/1993 | |
| EP | 0887348 A1 | 12/1998 | |
| EP | 1277738 A1 | 1/2003 | |
| EP | 1724267 A1 | 11/2006 | |
| EP | 2508510 A1 | 10/2012 | |
| EP | 2813506 A1 | 12/2014 | |
| JP | H11302254 A | 11/1999 | |
| JP | 2002/255964 A | 9/2002 | |
| JP | 2003 313126 A | 11/2003 | |
| JP | 2004-002826 A | 1/2004 | |
| JP | 2008542428 A | 11/2008 | |
| JP | 2012508223 A | 4/2012 | |
| JP | 2001139550 A | 5/2013 | |
| JP | 2014503535 A | 2/2014 | |
| WO | WO-1997/40017 A2 | 10/1997 | |
| WO | WO-99/00381 A1 | 1/1999 | |
| WO | WO-2001/083456 A1 | 11/2001 | |
| WO | WO-2002/002551 A1 | 1/2002 | |
| WO | WO-2002/034748 A1 | 5/2002 | |
| WO | WO-2002/085400 A1 | 10/2002 | |
| WO | WO-2003/075929 A1 | 9/2003 | |
| WO | WO-2004/072047 A1 | 8/2004 | |
| WO | WO-2005-118539 A1 | 12/2005 | |
| WO | WO-2006/037335 A2 | 4/2006 | |
| WO | WO-2006/046035 A1 | 5/2006 | |
| WO | WO-2006/088949 | 8/2006 | |
| WO | WO-2006/127587 A1 | 11/2006 | |
| WO | WO-2006/131484 | 12/2006 | |
| WO | WO-2007/050348 A2 | 5/2007 | |
| WO | WO-2007/084667 A2 | 7/2007 | |
| WO | WO-2007/085540 A1 | 8/2007 | |
| WO | WO-2007/122410 A1 | 11/2007 | |
| WO | WO-2007/127183 A1 | 11/2007 | |
| WO | WO-2008/007780 A1 | 1/2008 | |
| WO | WO-2008/033746 | 3/2008 | |
| WO | WO-2008/055068 A2 | 5/2008 | |
| WO | WO-2008/062201 A1 | 5/2008 | |
| WO | WO-2008/094992 A2 | 8/2008 | |
| WO | WO-2008/137270 A1 | 11/2008 | |
| WO | WO-2008/139987 A1 | 11/2008 | |
| WO | WO-2008/145688 A2 | 12/2008 | |
| WO | WO-2008/150827 A1 | 12/2008 | |
| WO | WO-2009/063240 A1 | 5/2009 | |
| WO | WO-2009/137462 A2 | 11/2009 | |
| WO | WO-2010/015520 A1 | 2/2010 | |
| WO | WO-2010/037765 A2 | 4/2010 | |
| WO | WO-2010/052569 A2 | 5/2010 | |
| WO | WO-2010/086646 A1 | 8/2010 | |
| WO | WO-2011/021038 A1 | 2/2011 | |
| WO | WO-2012/045804 A1 | 4/2012 | |
| WO | WO-2012/082997 A1 | 6/2012 | |
| WO | WO-2012/106343 A2 | 8/2012 | |
| WO | WO-2012/136722 A1 | 10/2012 | |
| WO | WO-2013/052110 A1 | 4/2013 | |
| WO | WO-2013/052613 A1 | 4/2013 | |
| WO | WO-2013/088404 A1 | 6/2013 | |
| WO | WO-2013/095060 A1 | 6/2013 | |
| WO | WO-2013/132270 A1 | 9/2013 | |
| WO | WO-2014/032019 A2 | 2/2014 | |
| WO | WO-2014/072714 A1 | 5/2014 | |
| WO | WO-2014/072937 A1 | 5/2014 | |
| WO | WO-2014/100227 A1 | 6/2014 | |
| WO | WO-2014/139465 A1 | 9/2014 | |
| WO | WO-2014/153280 A1 | 9/2014 | |
| WO | WO-2014/181137 A1 | 11/2014 | |
| WO | WO-2015/121657 A1 | 8/2015 | |
| WO | WO-2016/031815 A1 | 3/2016 | |
| WO | WO-2016/067038 A1 | 5/2016 | |
| WO | WO-2016067040 A1 | 5/2016 | |
| WO | WO-2017/208032 A1 | 12/2017 | |
| WO | WO-2017/222950 A1 | 12/2017 | |
| WO | WO-2017/222951 A1 | 12/2017 | |
| WO | WO-2017/222952 A1 | 12/2017 | |

OTHER PUBLICATIONS

Anonymous, 'CAS Registration No. RN-1257852-06-4 for Glycine, N-1H-imadazol-1-yl-N-3-pyridazinyl,' Dec. 29, 2010 (Dec. 29, 2010), CAS Registry, Chemical Abstracts Service, American Chemical Society, Columbus, OG (Publ), pp. 1, XP-002751578.

Anonymous, Chemcats, Accession No. 0056415163, for '1,6-Naphthyridine, 7-(3-methylphenyl)-5-(4-morpholinyl)-' Apr. 22, 2011 (Apr. 22, 2011), CAS Registry No. 1214393-37-9, Chemical Abstracts Service, American Chemical Society, Columbus, OH (Publ), pp. 1, XP-002643660.

Anonymous, Chemcats, Accession No. 0056415178, for '1,6-Naphthyridine, 5-(4-morpholinyl)-7-(2-pyridinyl)-,' Apr. 22, 2011 (Apr. 22, 2011), CAS Registry No. 1214438-02-4, Chemical Abstracts Service, American Chemical Society, Columbus, OH (Publ), pp. 1, XP-002643660.

Anonymous, PubChem, '3-(1H-Indol-3-yl)-3-(pyridin-4-yl)propionic acid—Compound Summary,' CID 4715104, AC1NFWP0, MolPort-000-861-678, BBL022406, STK895679, AKOS000266205, MCULE-7014658967, 3-(1H-indol-3-yl)-3-pyridin-3-ylpropanoic acid, Sep. 17, 2005 (Sep. 17, 2005), National Center for Biotechnology Information, U.S. National Library of Medicine, Bethesda, MD (Publ), pp. 1-6 XP-002718389.

Anonymous, PubChem, '3-(1H-Indol-3-yl)-3-pyridin-4-yl-propionic acid-Compound,' CID 3157817, ST073698 3-(1H-indol-3-yl)-3-pyridin-4-ylpropanoic acid, 3-(1H-indol-3-yl)-3-(pyridin-4-yl)propanoic acid, Aug. 10, 2005 (Aug. 10, 2005), National Center for Biotechnology Information, U.S. National Library of Medicine, Bethesda, MD (Publ), pp. 1-7 XP-002718387.

Anonymous, PubChem, 'AC1LLZ4B—Compound Summary,' CID 1092973, (3S)-3-(1H-indol-3-yl)-3-pyridin-4-ylpropanoic acid, Jul. 10, 2005 (Jul. 10, 2005), National Center for Biotechnology Information, U.S. National Library of Medicine, Bethesda, MD (Publ), pp. 1-5 XP-002718385.

Anonymous, PubChem, 'AC1LLZ4D—Compound Summary,' CID 1092974, (3R)-3-(1H-indol-3-yl)-3-pyridin-4-ylpropanoic acid,' Jul. 10, 2005 (Jul. 10, 2005), National Center for Biotechnology Information, U.S. National Library of Medicine, Bethesda, MD (Publ), pp. 1-5 XP-002718386.

Anonymous, PubChem, 'CID 40480236—Compound Summary,' CID 40480236, (3R)-3-(1H-indol-3-yl)-3-pyridin-3-ylpropanoic acid, May 30, 2009 (May 30, 2009), National Center for Biotechnology

(56) References Cited

OTHER PUBLICATIONS

Information, U.S. National Library of Medicine, Bethesda, MD (Publ), pp. 1-4 XP-002718391.
Anonymous, PubChem, 'ethyl 2 [pyridine-4-yl(pyrrol-1-yl)amino]acetate; hydrochloride,' CID 67857985, Nov. 30, 2012 (Nov. 30, 2012), National Center for Biotechnology Information, U.S. National Library of Medicine, Bethesda, MD (Publ), pp. 1-5 XP-002718393.
Anonymous, PubChem, 'SureCN2072816—Compound Summary,' CID 58088407, 3-(4-methoxy-1H-indol-3-yl)-3-pyridin-4-ylpropanoic acid, Aug. 19, 2012 (Aug. 19, 2012), National Center for Biotechnology Information, U.S. National Library of Medicine, Bethesda, MD (Publ), pp. 1-5 XP-002718392.
Anonymous, PubChem, 'SureCN9469183—Compound Summary,' CID 14373294, ethyl 2-[pyridine-4-yl(pyrrol-1-yl)amino]acetate, Feb. 9, 2007 (Feb. 9, 2007), National Center for Biotechnology Information, U.S. National Library of Medicine, Bethesda, MD (Publ), pp. 1-5 XP-002718390.
Assem el-SK et al., 'Effects of a Section of Histone Deacetylase Inhibitors on Mast Cell Activation and Airway and Colonic Smooth Muscles Contraction,' Int Immunopharmacol, Dec. 20, 2008 (Dec. 20, 2008) Sep. 19, 2008 (Sep. 19, 2008)(ePub), 8(13-14):1793-801.
Bouchecareilh M et al., 'Histone Deactylase Inhibitor (HDACi) Suberoylanilide Hydroxamic Acid (SAHA)-Mediated Correction of alpha1-Antitrypsin Deficiency,' J Biol Chem, Nov. 2, 2012 (Nov. 2, 2012) Sep. 20, 2012 (Sep. 20, 2012)(ePub), 287(45):38265-78.
Bruijnincx PC et al., 'Modeling the 2-His-1-carboxylate Facial Triad: Iron-catecholato Complexes as Structural and Functional Models of the Extrodiol Cleaving Dioxygenases,' J Am Chem Soc, Feb. 28, 2007 (Feb. 28, 2007) Feb. 1, 2007 (Feb. 1, 2007)(ePub), 129(8):2275-86.
Ciarlo E et al., 'Epigenetics in Sepsis: Targeting Histone Deacetylases,' Int J Antimicrob Agents, Jun. 2013 (Jun. 2013) May 9, 2013 (May 9, 2013)(ePub), 42(Supp):S8-12.
Clarke JD et al., 'Differential Effects of Sulforaphane on Histone Deacetylases, Cell Cycle Arrest and Apoptosis in Normal Prostate Cells Versus Hyperplastic and Cancerous Prostate Cells,' Mol Nutr Food Res, Jul. 2011 (Jul. 2011) Mar. 4, 2011 (Mar. 4, 2011)(ePub), 55(7):999-1009.
Crisanti MC et al., 'The HDAC Inhibitor Panobinostat (LBH589) Inhibits Mesothelioma and Lung Cancer Cells in vitro and in vivo with Particular Efficacy for Small Cell Lung Cancer,' Mol Cancer Ther, Aug. 2009 (Aug. 2009) Aug. 11, 2009 (Aug. 11, 2009)(ePub), 8(8):2221-31.
Cuadro AM et al., 'Synthesis of Highly Stabilised Ylides from N-[2-(1,3-Bensazolylmethyl)] Pyridinium Salts,' Tetrahedron, Jan. 1990 (Jan. 1990), 46(17):6033-46.
Djabali K and Christiano AM, 'Hairless Contains a Novel Nuclear Matrix Targeting Signal and Associates with Histone Deacetylase 3 in Nuclear Speckles,' Differentiation, Oct. 2004 (Oct. 2004), 72(8):410-8.
Downes JM et al., 'Biological Analogs. Spectroscopic Characteristics of Mercato- and Disulfide-Copper (II) Coordination in Relation to Type I Proteins,' Inorg Chem, Apr. 1981 (Apr. 1981), 20(4):1081-6.
Díez-Barra E et al., 'Double Michael Addition of Azoles to Methyl Propiolate: A Straightforward Entry to Ligands With Two Heterocyclic Rings,' Tetrahedron Lett, Aug. 7, 2004 (Aug. 7, 2004)(ePub), 45(2004):6937-9.
Elslager et al., "Synthesis of 5,5'[[[3-(dimethylamino)propyl]imino]]bis[3-(trichloromethyl)-1,2,4-thiadiazole] and related thiadiazoles as antimalarial agents." Journal of Heterocyclic Chemistry 1973, 10, 611-622.
Ferrara N and Alitalo K, 'Clinical Applications of Angiogenic Growth Factors and Their Inhibitors,' Nat Med, Dec. 1999 (Dec. 1999), 5(12):1359-64.
Galardon E et al., 'Modeling the Inhibition of Peptide Deformylase by Hydroxamic Acids: Influence of the Sulfur Donor,' Daltron Trans, Mar. 14, 2007 (Mar. 14, 2007) Jan. 23, 2007 (Jan. 23, 2007)(ePub), (10):1047-52.

Giannini G et al., 'Exploring bis-(indolyl)methane Moiety as an Alternative and Innovative CAP Group in the Design of Histone Deacetylase (HDAC) Inhibitors,' Bioorg Med Chem Lett, May 15, 2009 (May 15, 2009) Mar. 26, 2009 (Mar. 26, 2009)(ePub), 19(10): 2840-3.
Gillespie J et al., 'Histone Deacetylases are Dysregulated in Rheumatoid Arthritis and a Novel Histone Deacetylase 3-Selective Inhibitor Reduces Interleukin-6 Production by Peripheral Blood Mononuclear Cells from Rheumatoid Arthritis Patients,' Arthritis Rheum, Feb. 2012 (Feb. 2012), 64(2):418-22.
Govindarajan N et al., 'Reducing HDAC6 Ameliorated Cognitive Deficits in Mouse Model for Alzheimer's Disease,' EMBO Mol Med, Jan. 2013 (Jan. 2013) Nov. 26, 2012 (Nov. 26, 2013)(ePub), 5(1):52-63.
Grattagliano I et al., 'Glutathione Peroxidase, Thioredoxin, and Membrane Protein Changes in Erythrocytes Predict Ribavirin-Induced Anemia,' Clin Pharmacol Ther, Oct. 2005 (Oct. 2005), 78(4):422-32.
Gryder BE at al., 'Histone Deacetylase Inhibitors Equipped with Estrogen Receptor Modulation Activity,' J Med Chem, Jul. 25, 2013 (Jul. 25, 2013) Jul. 3, 2013 (Jul. 3, 2013)(ePub), 56(14):5782-96.
Hancock WW et al., 'HDAC Inhibitor Therapy in Autoimmunity and Transplantation,' Ann Rheum Dis, Apr. 2012 (Apr. 2012), 71(Supp 2):i46-54.
Haquette P et al., 'Synthesis of N-Functionalized 2,2'-dipyridylamine Ligands, Complexation to Ruthenium (II) and Anchoring of Complexes to Papain from Papaya Latex,' J Organomet Chem, Mar. 15, 2009 (Mar. 15, 2009), 694(6):937-41.
Hawtree S et al., 'The Role of Histone Deacetylases in Rheumatoid Arthritis Fibroblast-like Synoviocytes,' Biochem Soc Trans, Jun. 2013 (Jun. 2013), 41(3):783-8.
Hayakawa M et al., 'Synthesis and Biological Evaluation of pyrido[3',2':4,5]furo[3,2-d] Pyrimidine Derivatives as Novel PI3 Kinasae p110alpha Inhibitors,' Bioorg Med Chem Lett, May 1, 2007 (May 1, 2007) Feb. 15, 2007 (Feb. 15, 2007)(ePub), 17(9):2438-42.
Hebbel RP et al., 'The HDAC Inhibitors Trichostatin A and Suberoylanalide Hydroxamic Acid Exhibit Multiple Modalities of Benefit for the Vascular Pathobiology of Sickle Transgenic Mice,' Blood, Mar. 25, 2010 (Mar. 25, 2010) Jan. 6, 2010 (Jan. 6, 2010), 115(12):2483-90.
Imesch P et al., 'Romidepsin Reduces Histone Deacetylase Activity, Induces Acetylation of Histones, Inhibits Proliferation, and Activates Apoptosis in Immortalized Epithelial Endometriotic Cells,' Fertil Steril, Dec. 2010 (Dec. 2010) Jun. 3, 2010 (Jun. 3, 2010)(ePub), 94(7):2838-42.
International Searching Authority, International Preliminary Report on Patentability (Form IB/373) and Written Opinion (Form ISA/237) for International Application No. PCT/GB2010/050116 (Form ISA/210), (Beligny S), completed on Apr. 27, 2012 (Apr. 27, 2012) and dated Aug. 2, 2011 (Aug. 2, 2011), pp. 1-11.
International Searching Authority, International Preliminary Report on Patentability (Form IB/373) and Written Opinion (Form ISA/237) for International Application No. PCT/GB2010/051370 (Form ISA/210), (Helps I), completed on Oct. 28, 2010 (Oct. 28, 2010) and dated Feb. 21, 2012 (Feb. 21, 2012), pp. 1-6.
International Searching Authority, International Preliminary Report on Patentability (Form IB/373) and Written Opinion (Form ISA/237) for International Application No. PCT/GB2011/050824 (Form ISA/210), (Marzi E), completed on Jun. 27, 2011 (Jun. 27, 2011) and dated Nov. 6, 2012 (Nov. 6. 2012), pp. 1-7.
International Searching Authority, International Preliminary Report on Patentability (Form IB/373) and Written Opinion (Form ISA/237) for International Application No. PCT/GB2013/050583 (Form ISA/210), (Wolf C), completed on Apr. 11, 2013 (Apr. 11, 2013) and dated Sep. 9, 2014 (Sep. 9, 2014), pp. 1-6.
International Searching Authority, International Preliminary Report on Patentability (Form IB/373) and Written Opinion (Form ISA/237) for International Application No. PCT/GB2013/052917 (Form ISA/210), (Sotoca Usina E), completed on Jan. 8, 2014 (Jan. 8, 2014) and dated May 12, 2015 (May 12, 2015), pp. 1-11.
International Searching Authority, International Preliminary Report on Patentability (Form IB/373) and Written Opinion (Form ISA/237) for International Application No. PCT/GB2014/051454 (Form

(56) References Cited

OTHER PUBLICATIONS

ISA/210), (Sotoca Usina E), completed on Jun. 10, 2014 (Jun. 10, 2014) and dated Nov. 10, 2015 (Nov. 10, 2015), pp. 1-7.
International Searching Authority, International Search Report for International Application No. PCT/GB2010/050116 (Form ISA/210), (Beligny S), completed on Apr. 27, 2012 (Apr. 27, 2012) and dated May 10, 2010 (May 10, 2010), pp. 1-6.
International Searching Authority, International Search Report for International Application No. PCT/GB2010/051370 (Form ISA/210), (Helps I), completed on Oct. 28, 2010 (Oct. 28, 2010) and dated Nov. 9, 2010 (Nov. 9, 2010), pp. 1-4.
International Searching Authority, International Search Report for International Application No. PCT/GB2011/050824 (Form ISA/210), (Marzi E), completed on Jun. 27, 2011 (Jun. 27, 2011) and dated Jul. 12, 2011 (Jul. 12, 2011), pp. 1-5.
International Searching Authority, International Search Report for International Application No. PCT/GB2013/050583 (Form ISA/210), (Wolf C), completed on Apr. 11, 2013 (Apr. 11, 2013) and dated May 6, 2013 (May 6, 2013), pp. 1-4.
International Searching Authority, International Search Report for International Application No. PCT/GB2013/052917 (Form ISA/210), (Sotoca Usina E), completed on Jan. 8, 2014 (Jan. 8, 2014) and dated Jan. 22, 2014 (Jan. 22, 2014), pp. 1-9.
International Searching Authority, International Search Report for International Application No. PCT/GB2014/051454 (Form ISA/210), (Sotoca Usina E), completed on Jun. 10, 2014 (Jun. 10, 2014) and dated Jun. 17, 2014 (Jun. 17, 2014), pp. 1-4.
International Searching Authority, International Search Report for International Application No. PCT/GB2015/053256 (Form ISA/210), (Ladenburger C), completed on Nov. 26, 2015 (Nov. 26, 2015) and dated Dec. 8, 2015 (Dec. 8, 2015), pp. 1-7.
International Searching Authority, International Search Report for International Application No. PCT/GB2015/053260 (Form ISA/210), (Ladenburger C), completed on Nov. 30, 2015 (Nov. 30, 2015) and dated Dec. 9, 2015 (Dec. 9, 2015), pp. 1-9.
International Searching Authority, Written Opinion (Form ISA/237) for International Application No. PCT/GB2015/053256 (Form ISA/210), (Ladenburger C), completed on Nov. 26, 2015 (Nov. 26, 2015) and dated Dec. 8, 2015 (Dec. 8, 2015), pp. 1-6.
International Searching Authority, Written Opinion (Form ISA/237) for International Application No. PCT/GB2015/053260 (Form ISA/210), (Ladenburger C), completed on Nov. 30, 2015 (Nov. 30, 2015) and dated Dec. 9, 2015 (Dec. 9, 2015), pp. 1-7.
Kato K et al., 'Thromboxane Synthetase Inhibitors (TXSI). Design, Synthesis, and Evaluation of Novel Series of Omega-Pyridylalkenoic Acids,' J Med Chem, Mar. 1985 (Mar. 1985), 28(3):287-94.
Kazantsev AG and Thompson LM, 'Therapeutic Application of Histone Deacetylase Inhibitors for Central Nervous System Disorders,' Nat Rev Drug Discov, Oct. 2008 (Oct. 2008), 7(10):854-68.
Kim MG et al., 'The Relationship Between Cisplatin Resistance and Histone Deacetylase Isoform Overexpression in Epithelial Ovarian Cancer Cell Lines,' J Gynecol Oncol, Jul. 2012 (Jul. 2012) Jul. 2, 2012 (Jul. 2, 2012)(ePub), 23(3):182-9.
Kirin SI et al., 'Synthesis and Characterization of CuII Complexes with Amino Acid Substituted di(2-pyridyl)amine Ligands,' Eur J Inorg Chem, Jun. 22, 2007 (Jun. 22, 2007)(ePub), 2007(23):3686-94.
Kovacs J and Mokhir A, 'Nucleic Acid Controlled Catalysts of Carboxylic Esters Hydrolysis,' Bioorg Med Chem Lett, Nov. 1, 2008 (Nov. 1, 2008) Sep. 27, 2008 (Sep. 27, 2008)(ePub), 18(21):5722-4.
Kovalskiy DA and Perevalov VP, 'Synthesis of 7-(3-piperidyl)-[1,6]naphthyridine and 7-(4-pipe-ridyl)[1,6]naphthyridine,' Chem Hetercycl Comp, Nov. 24, 2009 (Nov. 24, 2009)(ePub), 45(9):1053-7 ISSN:0009-3122.
Kuendgen A et al., 'Treatment of Poor-Risk Myelodysplastic Syndromes and Acute Myeloid Leukemia with a Combination of 5-Azacytidine and Valproic Acid,' Clin Epigenetics, Aug. 2011 (Aug. 2011) Apr. 8, 2011 (Apr. 8, 2011)(ePub), 2(2):389-99.

Lee et al., "Synthesis and photophysical properties of five-membered ring π-conjugated materials based on bisthiazol-2-yl-amine and their metal complexation studies." Tertahedron. 2010, 66, 9440-9444.
Lee SU et al., 'In vitro and in vivo Osteogenic Activity of Largazole,' ACS Med Chem Lett, Mar. 10, 2011 (Mar. 10, 2011), 2(3):248-51.
Lemon DD et al., 'Cardiac HDAC6 Catalytic Activity is Induced in Response to Chronic Hypertension,' J Mol Cell Cardiol, Jul. 2011 (Jul. 2011) Apr. 23, 2011 (Apr. 23, 2011)(ePub), 51(1):41-50.
Lu W et al., 'Pd-Catalyzed Selective Addition of Heteroaromatic C—H Bonds to C—C Triple Bonds Under Mild Conditions,' Org Lett, Sep. 21, 2000 (Sep. 21, 2000), 2(19):2927-30.
Mai A et al., 'Identification of two new Synthetic Histone Deacetylase Inhibitors that Modulate Globin Gene Expression in Erythroid Cells from Healthy Donors and Patients with Thalassemia,' Mol Pharamcol, Nov. 2007 (Nov. 2007) Jul. 31, 2007 (Jul. 31, 2007)(ePub), 72(5):1111-23.
McGraw AL, 'Romidepsin for the Treatment of T-cell Lymphomas,' Am J Health Syst Pharm, Jul. 1, 2013 (Jul. 1, 2013), 70(13):1115-22.
McKinsey TA, 'The Biology and Therapeutic Implications of HDACs in the Heart,' Handb Exp Pharmacol, 2011 (2011), 206:57-78.
Meredith EL et al., 'Identification of Orally Available Naphthyridine Protein Kinase D Inhibitors,' J Med Chem, Aug. 12, 2010 (Aug. 12, 2010), 53(15):5400-21.
Moradei O et al., 'Histone Deacetylase Inhibitors in Cancer Therapy: New Compounds and Clinical Update of Benzamide-type Agents,' Curr Top Med Chem, 2008 (2008), 8(10):841-58.
Mull RP et al., 'Antihypertensively Active Amidoximes,' J Am Chem Soc, Jul. 1, 1958 (Jul. 1, 1958), 80(14):3769-72.
Nemenoff R, 'Wound Healing: A Role for HDACs in Inhibition of Fibroblast Proliferation Through Repression of PDGF Receptor-alpha. Focus on Repression of PDGF-R-alpha After Cellular Injury Involves TNF-alpha Formation of a c-Fos-YY1 Complex, and Negative Regulation by HDAC,' Am J Physiol Cell Physiol, Jun. 1, 2012 (Jun. 1, 2012) Mar. 28, 2012 (Mar. 28, 2012)(ePub), 302(11):C1588-9.
Ohashi A et al., 'Covalent Linking of Coordination-Organized Slipped Cofacial Porphyrin Dimers,' Bull Chem Soc Jpn, Feb. 10, 2004 (Feb. 10, 2004)(ePub), 77(2004):365-74.
Oyamada J and Kitamura T, 'Pt(II)-Catalyzes Hydroarylation Reaction of Alkynes with Pyrroles and Furans,' Tetrahedron, Mar. 14, 2009 (Mar. 14, 2009)(ePub), 65(2009):3842-7.
Patra N et al., 'A Novel Histone Deacetylase (HDAC) Inhibitor MHY219 Induces Apoptosis via Up-Regulation of Androgen Receptor Expression in Human Prostate Cancer Cells,' Biomed Pharmacother, Jun. 2013 (Jun. 2013) Feb. 16, 2013 (Feb. 16, 2013)(ePub), 67(5):407-15.
Peters L et al., 'Synthesis and Transition Metal Complexes of 3,3-bis(1-vinylimidazol-2-yl)propionic Acid, A New N,N,O Ligand Suitable for Copolymerisation,' Inorg Chim Acta, Mar. 12, 2011 (Mar. 12, 2011), 374(2011):392-40.
Peters L et al., 'The New Facial Tripod Ligand 3,3-bis(1-methylimidazol-2-yl)propionic Acid and Carbonyl Complexes Thereof Containing Manganese and Rhenium,' J Organomet Chem, Nov. 25, 2004 (Nov. 25, 2004), 690(2005):2009-16.
Pham TX and Lee J, 'Dietary Regulation of Histone Acetylases and Deacetylases for the Prevention of Metabolic Diseases,' Nutrients, Nov. 28, 2012 (Nov. 28, 2012), 4(12):1868-86.
Piscopo M et al., 'H3 and H3.3 Histone mRNA Amounts and Ratio in Oral Squamous Cell Carcinoma and Leukoplakia,' Oral Dis, Mar. 2006 (Mar. 2006), 12(2):130-6.
Price S and Dyke HJ, 'Histone Deacetylase Inhibitors: An Analysis of Recent Patenting Activity,' Exp Opin Therap Patents, Aug. 7, 2007 (Aug. 7, 2007)(ePub), 17(7):745-65.
Richardson PG et al., 'Preclinical Data and Early Clinical Experience Supporting the Use of Histone Deacetylase Inhibitors in Multiple Myeloma,' Leuk Res, Jul. 2013 (Jul. 2013) Apr. 9, 2013 (Apr. 9, 2013), 37(7):829-37.
Rotili D et al., 'Non-Cancer Uses of Histone Deacetylase Inhibitors: Effects on Infectious Diseases and beta-Hemoglobinopathies,' Curr Top Med Chem, 2009 (2009), 9(3):272-91.

(56) References Cited

OTHER PUBLICATIONS

Safdy ME et al., 'Tryptophan Analogues. 1. Synthesis and Antihypertensive Activity of Positional Isomers,' J Med Chem, Jun. 1982 (Jun. 1982), 25(6):723-30.
Saifuddin M et al., 'Water-Accelerated Cationic ?-(7-endo) Cyclisation: Application to Indole-Based Peri-Annulated Polyheterocycles,' Eur J Org Chem, Sep. 2010 (Sep. 2010) Jul. 20, 2010 (Jul. 20, 2010)(ePub), 2010(26):5108-17.
Shanmugam MK and Sethi G, 'Role of Epigenetics in Inflammation-Associated Diseases,' Subcell Biochem, 2013 (2013), 61:627-57 (PubMed Abstract only).
Singh B et al., 'Novel cAMP PDE III Inhibitors: 1,6-naphthyridin-2(1H)-ones,' J Med Chem, Dec. 25, 1992 (Dec. 25, 1992), 35(26):4858-65.
Singh J et al., 'HDAC Inhibitor SAHA Normalizes the Levels of VLCFAs in Human Skin Fibroblasts from X-ALD Patients and Downregulates the Expression of Proinflammatory Cytokines in Abcd1/2-Silenced Mouse Astrocytes,' J Lipid Res, Nov. 2011 (Nov. 2011) Sep. 4, 2011 (Sep. 4, 2011)(ePub), 52(11):2056-69.
Somei et al. "Boronation-thallation, a new approach to the synthesis of indoles having aryl, and/or a heteroaryl substituent at the 4-position." Chem. Pharm. Bull. 34(9), 3971-3973, (1986).
Su GH et al., 'A Novel Histone Deacetylase Inhibitor Identified by High-Throughput Transcriptional Screening of a Compound Library,' Cancer Res, Jun. 15, 2000 (Jun. 15, 2000), 60(12):3137-42.
Suzuki T et al., 'Identification of G Protein-Coupled Receptor 120-Selective Agonists Derived from PPARgamma Agonists,' J Med Chem, Dec. 11, 2008 (Dec. 11, 2008), 51(23):7640-4.
Torrioli M et al., 'Treatment with Valproic Acid Ameliorates ADHD Symptoms in Fragile X Syndrome Boys,' Am J Med Genet A, Jun. 2010 (Jun. 2010), 152A(6):1420-7.
Usui S et al., 'Design, Synthesis, and Biological Activity of Novel PPARgamma Ligands Based on Rosiglitazone and 15d-PGJ2,' Bioorg Med Chem Lett, Mar. 15, 2005 (Mar. 15, 2005), 15(6):1547-51.
Van Damme M et al., 'HDAC Isoenzyme Expression is Deregulated in Chronic Lymphocytic Leukemia B-Cells and has a Complex Prognostic Significance,' Epigenetics, Dec. 1, 2012 (Dec. 1, 2012) Oct. 29, 2012 (Oct. 29, 2012), 7(12):1403-12.
Yamamoto T et al., 'Structure-Activity Relationship Study of 1,4-dihydropyridine Derivatives Blocking N-type Calcium Channels,' Bioorg Med Chem Lett, Feb. 15, 2006 (Feb. 15, 2006) Nov. 23, 2005 (Nov. 23, 2005)(ePub), 16(4):798-802.
Ye J, 'Improving Insulin Sensitivity with HDAC Inhibitor,' Diabetes, Mar. 2013 (Mar. 2013), 62(3):685-7.
Zakeeruddin SM et al., 'Glucose Oxidase Mediation by Soluble and Immobilized Electroactive Detergents,' Biosens Bioelectron, 1996 (1996), 11(3):305-15.
Zhang L et al., 'Inhibition of Histone Deacetylase-Induced Myocardial Repair is Mediated by c-Kit in Infarcted Hearts,' J Biol Chem, Nov. 16, 2012 (Nov. 16, 2012) Sep. 28, 2012 (Sep. 28, 2012)(ePub), 287(47):39338-48.
Lobera et al., "Selective class IIa deacetylase inhibition via a nonchelating zinc-binding group." Nat. Chem. Biol. 2013, 9, 319-325.
Falkenberg et al. Nature Reviews Drug Discovery, vol. 13, 673-691, 2014.
Madsen et al. The effect of various zinc binding groups on inhibition of histone deacetylases 1-11. ChemMedChem Mar. 27, 2014;9(3):614026. Epub Dec. 27, 2013.
U.S. Appl. No. 15/888,646, Scriptaid Isosteres and Their Use in Therapy, Feb. 5, 2018, Pending.
Bush; Circulation Research 2010, 106, 272-284. (Year: 2010).
Dietz; Pharmacological Research 2010, 62, 11-17. (Year: 2010).
Grayson; Molecular Pharmacology Feb. 2010, 77, 126-135. (Year: 2010).

Kantharaj; "Histone Deacetylase Inhibitors as Therapeutic Agents for Cancer Therapy: Drug Metabolism and Pharmacokinetic Properties" Chapter 5: Drug Development—A Case Study Based Insight into Modern Strategies, pp. 101-120, Intech (Dec 2011). (Year: 2011).
Pang; Journal of Pharmacology and Experimental Therapeutics Nov. 2010, 335, 266-272. (Year: 2010).
Xu; Oxidative Medicine and Cellular Longevity 2011, 5 pages. doi: 10.1155/2011/143269 (Year: 2011).
Uno, S., et al, "N2-N1 Migration of s-Triazinyl Group in the Reaction of N1-Acetyl-N2-(s-triazinyl)alkylenediamines", Bulletin of the Chemical Society of Japan, 1973, 46(7), 2257-8.
Bazzaro et al., "Ubiquitin Proteasome System Stress Underlies Synergistic Killing of Ovarian Cancer Cells by Bortezomib and a Novel HDAC6I Inhibitor," Clinical Cancer Research, 14(22):7340-7347, Nov. 15, 2008.
Hanke et al., "Carfilzomib combined with suberanilohydroxamic acid (SAHA) synergistically promotes endoplasmic reticulum stress in non-small cell lung cancer cell lines," J. Cancer Res. Clin Oncol, 142(3):549-560, Sep. 18, 2015.
Hideshima et al., "Small-molecule inhibition of proteasome and aggresome function induces synergistic antitumor activity in multiple myeloma," PNAS, National Academy of Sciences, US, 102(24):8567-8572, Jun. 14, 2005.
International Searching Authority, International Search Report (Form ISA/210) for International Application No. PCT/GB2017/051619, completed on Jul. 26, 2017 and dated Oct. 18, 2017, pp. 1-9.
International Searching Authority, Written Opinion (Form ISA/237) for International Application No. PCT/GB2017/051619, completed on Jul. 26, 2017 and dated Oct. 18, 2017, pp. 1-16.
Jagannath et al., "Combined proteasome and histone deacetylase inhibition: A promising synergy for patients with relapsed/refractory multiple myeloma," Leukemia Research 34(9):1111-1118, Sep. 1, 2010.
San-Miguel et al., "A Phase IB, Multi-Center, Open-Label Dose-Escalation Study of Oral Panobinostat (LBH589) and I.V. Bortezomib in Patients with Relapsed Multple Myeloma," Internet Citation, Dec. 7, 2009, 4 pages.
Santo et al., "Preclinical activity, pharmacodynamic, and pharmacokinetic properties of a selective HDAC6 inhibitor, ACY-1215, in combination with bortezomib in multiple myeloma," Blood, 119(11):2579-2589, Mar. 15, 2012.
Schafer et al., "Pyridylalanine-Containing Hydroxamic Acids as Selective HDAC6 Inhibitors," ChemMedChem 4:283-290 (2009).
U.S. Appl. No. 16/304,789, Combinations Comprising Histone Deacetylase Inhibitors, Nov. 27, 2018, Pending.
U.S. Appl. No. 13/145,250, Scriptaid Isosteres and Their Use in Therapy, filed Aug. 30, 2011, Issued as U.S. Pat. No. 8,748,458 on Jun. 10, 2014.
U.S. Appl. No. 14/266,197, Scriptaid Isosteres and Their Use in Therapy, filed Apr. 30, 2014, Issued as U.S. Pat. No. 9,340,503 on May 17, 2016.
U.S. Appl. No. 15/095,829, Scriptaid Isosteres and Their Use in Therapy, filed Apr. 11, 2016, Pending.
U.S. Appl. No. 14/441,401, Novel Histone Deacetylase Inhibitors and Their Use in Therapy, filed May 7, 2015 Issued as U.S. Pat. No. 9,676,765 on Jun. 13, 2017.
U.S. Appl. No. 15/589,491, Novel Histone Deacetylase Inhibitors and Their Use in Therapy, filed May 8, 2017, Pending.
U.S. Appl. No. 14/890,331, Novel Histone Deacetylase Inhibitors, filed Nov. 10, 2015, Allowed Published as US 2016-0096804 on Apr. 7, 2016.
U.S. Appl. No. 15/667,069, Novel Historic Deacetylase Inhibitors, filed Aug. 2, 2017, Pending.
U.S. Appl. No. 15/522,191, Polyheteroaryl Histone Deacetylase Inhibitors and Their Use in Therapy, filed Apr. 26, 2017, Pending.

* cited by examiner

DIHETEROARYL HISTONE DEACETYLASE INHIBITORS AND THEIR USE IN THERAPY

CROSS-REFERENCE TO RELATED APPLICATIONS

This application is the national stage of International (PCT) Patent Application Serial No. PCT/GB2015/053260, filed Oct. 29, 2015, which claims the benefit of and priority to Great Britain Patent Application No. 1419228.0, filed Oct. 29, 2014, the contents of each of which are hereby incorporated by reference in their entirety.

FIELD OF THE INVENTION

The present invention relates to novel compounds which are inhibitors of histone deacetylase (HDAC) and therefore have therapeutic utility.

BACKGROUND OF THE INVENTION

HDACs are zinc metalloenzymes that catalyse the hydrolysis of acetylated lysine residues. In histones, this returns lysines to their protonated state and is a global mechanism of eukaryotic transcriptional control, resulting in tight packaging of DNA in the nucleosome. Additionally, reversible lysine acetylation is an important regulatory process for non-histone proteins. Thus, compounds which are able to modulate HDAC have important therapeutic potential.

WO2010/086646 discloses compounds which act as inhibitors of HDAC. In the claims, L is defined broadly as being a "nitrogen-containing" heteroaryl. All the exemplified compounds require that L is pyridyl or benzofused pyridyl.

WO2014/072714 also discloses compounds which act has inhibitors of HDAC. However, WO2014/072714 has compounds with L and Y as capping groups, wherein at least one capping group must be a 5-membered nitrogen-containing heteroaryl.

SUMMARY OF THE INVENTION

It has surprisingly been found that replacing both L groups of the compounds disclosed in WO2010/086646 or L and Y in the compounds disclosed in WO2014/072714 with 5 to 12 membered heteroaryl groups containing two nitrogen atoms results in improved plasma clearance following IV dosing.

A compound of the formula

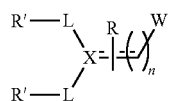

wherein:
⸺ is a double bond and X is C; or
⸺ is a single bond and X is N, CH or $CQR_1$; and
wherein:
n is 1 to 10;
R is H or $QR_1$;
each $R'$ is independently selected from H and $QR_1$;
each Q is independently selected from a bond, $C_1$-$C_4$ alkylene, CO, $CO_2$, NH, S, SO, $SO_2$ or O;
each $R_1$ is independently selected from H, $C_1$-$C_{10}$ alkyl, $C_2$-$C_{10}$ alkenyl, $C_2$-$C_{10}$ alkynyl, $C_1$-$C_4$ alkoxy, aryl, heteroaryl, $C_1$-$C_{10}$ cycloalkyl, halogen, $C_1$-$C_{10}$ alkylaryl, $C_1$-$C_{10}$ alkyl heteroaryl, $C_1$-$C_{10}$ heterocycloalkyl, $NR_2R_3$ or trifluoromethyl, wherein $R_2$ and $R_3$ are $C_1$-$C_4$ alkyl;
L is independently a 5 to 12 membered heteroaryl, wherein each L contains at least two nitrogen atoms;
W is a zinc-binding group;
each aryl or heteroaryl may be substituted by up to five substituents selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl; and
each alkyl, alkenyl or alkynyl may be optionally substituted with $C_1$-$C_{10}$ alkyl, $C_2$-$C_{10}$ alkenyl, $C_2$-$C_{10}$ alkynyl, aryl, cycloalkyl, heteroaryl, halogen, $NH_2$, $NO_2$ or hydroxyl, or a pharmaceutically acceptable salt thereof.

The compounds of the invention may be useful as an inhibitor of HDAC, i.e. in they may be used in a method of treating a disease associated with an over-expression of HDAC.

DESCRIPTION OF THE INVENTION

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene.

As used herein, "cycloalkyl" contains from 3 to 10 carbon atoms. It may be monovalent or divalent.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene.

As used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, $C_1$-$C_{10}$ alkyl may be $CF_3$, $CHF_2$, $CH_2CF_3$, $CH_2CHF_2$ or $CF_2CF_3$ or $OCF_3$, $OCHF_2$, $OCH_2CF_3$, $OCH_2CHF_2$ or $OCF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)

amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As will be appreciated from above, L is a 5- to 12-membered heteroaryl, wherein each L contains at least two nitrogen atoms. The 5- to 12-membered heteroaryl may be bicyclic, for example, a 6-membered heteroaryl fused to a 5-membered heteroaryl as shown in Examples B, C, G, K, N and P. In other words, bicyclic means that the two rings share two atoms.

In the compounds of the invention, certain L groups are substituted with R'. However, they may still be substituted by up to three additional substituents, selected from the groups defined above. It is preferred that R' is the only substituent.

As used herein, the term "heterocycle" or "heterocycloalkyl" is a mono- or di-valent carbocyclic radical containing up to 4 heteroatoms selected from oxygen, nitrogen and sulfur. It may be monocyclic or bicyclic. It is preferably saturated. The word 'linker' has been used herein to mean di-valent. If the heterocycle is a di-valent linker, the heterocycle may be attached to neighbouring groups through a carbon atom, or through on of the heteroatoms, e.g. a N. Examples of heterocycles are piperazine or morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo e.g. F, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix-ene. This means that the group is divalent, i.e. a linker group.

Preferred Groups of the Invention

The group W is a zinc-chelating residue, i.e. a metallophile capable of binding with zinc in the active site of HDAC. Suitable metallophiles are known to those skilled in the art.

In a preferred embodiment, W is selected from:

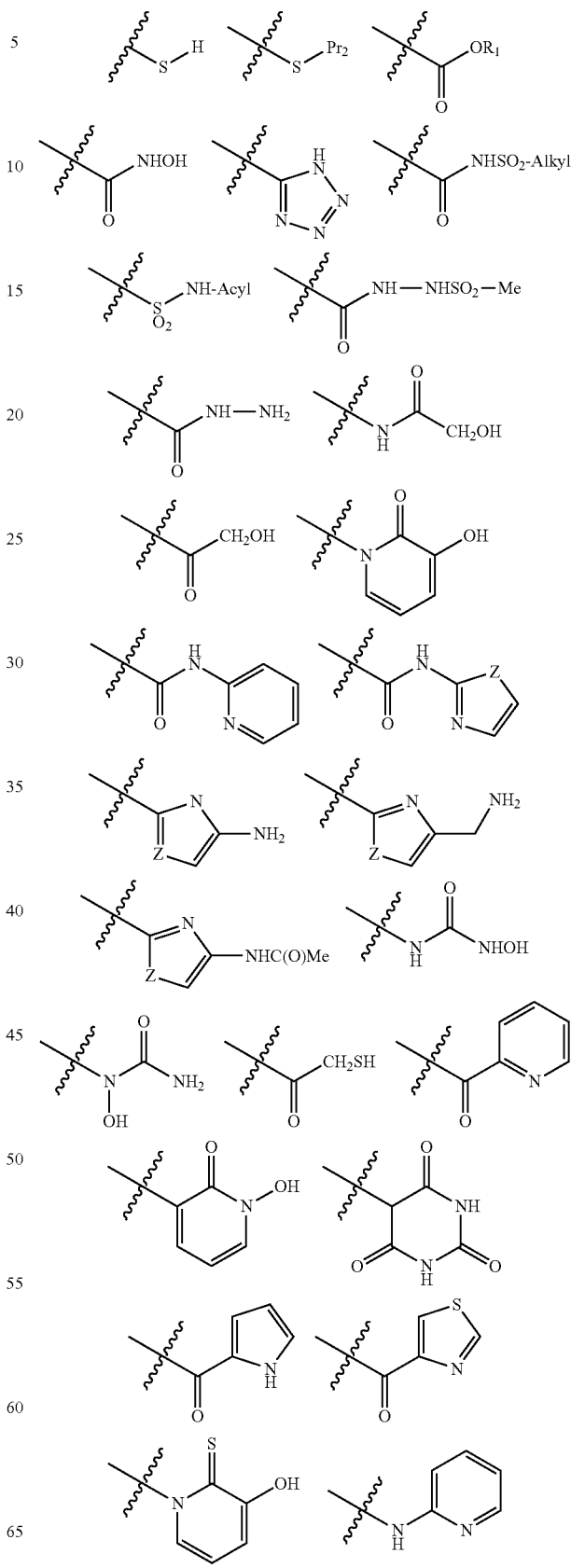

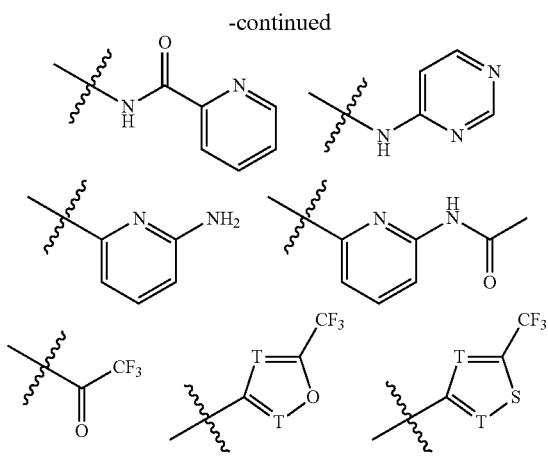

wherein $R_1$ is as defined in claim 1, $Pr^2$ is H or a thiol protecting group, Z is selected from O, S or NH and T is N or CH.

When W is $COOR_1$, $R_1$ is not halogen. More preferably, when W is $COOR_1$, $R_1$ is H or $C_1$-$C_{10}$ alkyl.

Preferably, W is COOMe, —CONHOH, —CONHSO$_2$CH$_3$, —CONHNHSO$_2$CH$_3$, —CONHNH$_2$, —CONH(2-pyridyl), —NHCONHOH, tetrazole, hydroxypyridin-2-thione or hydroxypyridin-2-one. Preferably W is not $COOR_1$. More preferably, W is —CONHOH, CONHSO$_2$CH$_3$, —CONHNHSO$_2$CH$_3$, —CONHNH$_2$, —CONH(2-pyridyl) —NHCONHOH, tetrazole, hydroxypyridin-2-thione or hydroxypyridin-2-one. Even more preferably, W is —CONHOH, tetrazole, hydroxypyridin-2-thione or hydroxypyridin-2-one. Most preferably, W is —CONHOH.

Preferably, at least one, preferably both L groups are independently selected from pyrazolyl, pyrazinyl, pyrimidinyl, pyridazinyl, thiadiazolyl and imidazolyl, each of which may be optionally fused to a 5-membered heteroaryl. Preferably, the 5-membered heteroaryl contains N or O, preferably N.

At least one, preferably both L is independently selected from pyrazolyl, pyrazinyl, pyrimidinyl, pyridazinyl, thiadiazolyl, oxadiazolyl and imidazolyl, each of which may be optionally fused to a 5-membered heteroaryl, wherein the 5-membered heteroaryl contains at least one N or O, preferably N.

More preferably, at least one, preferably both L is a 6-membered heteroaryl independently selected from pyrazinyl, pyrimidinyl, pyridazinyl. The 6-membered heteroaryl is optionally fused to a 5-membered heteroaryl, preferably a nitrogen-containing heteroaryl.

Preferably, at least one L is pyrazinyl. More preferably, each L is independently selected from pyrazinyl and pyridazinyl. More preferably still, one L is pyridazinyl and the other L is pyrazinyl.

Alternatively $R'$ is independently selected from H and $QR_1$;

each Q is independently selected from a bond, CO, CO$_2$, NH, S, SO, SO$_2$ or O;

each $R_1$ is independently selected from H, $C_1$-$C_{10}$ alkyl, $C_2$-$C_{10}$ alkenyl, $C_2$-$C_{10}$ alkynyl, aryl, heteroaryl, $C_1$-$C_{10}$ cycloalkyl, halogen, $C_1$-$C_{10}$ alkylaryl, $C_{10}$ alkyl heteroaryl, $C_1$-$C_{10}$ heterocycloalkyl, or trifluoromethyl.

Preferably, n is 3 to 7. More preferably, n is 6 or 7.

In a preferred embodiment, X⋯ is N- or, X⋯ is C═. Preferably, X⋯ is N.

At least one $R'$ may also be a substituted or unsubstituted aryl or O— (substituted or unsubstituted aryl). Preferably, at least one $R'$ is aryl or O-aryl, each of which may be substituted with a halogen, amino or $C_1$-$C_{10}$ alkyl. The aryl may be substituted in any position. The aryl may be mono-, bis-, or tri-substituted.

Most preferably, at least one $R'$ is selected from H, $C_1$-$C_{10}$ alkyl, O—($C_1$-$C_{10}$ alkyl), N($C_1$-$C_{10}$ alkyl)$_2$, heterocycloalkyl, trifluoromethyl or halogen, preferably wherein the alkyl is substituted with at least one fluorine.

Preferably, Q is a direct bond or —O—. More preferably, Q is a direct bond. Where Q is a direct bond, $R_1$ can be as defined for $R'$.

Alternatively, $R_1$ can be selected from halogen (preferably F, when Q is a direct bond), $C_1$-$C_{10}$ alkyl, $C_2$-$C_{10}$ alkenyl or $C_2$-$C_{10}$ alkynyl, preferably substituted with halogen, N($C_1$-$C_{10}$ alkyl)$_2$, NH$_2$, NO$_2$ or hydroxyl. More preferably, $R_1$ is $C_1$-$C_{10}$ alkyl substituted with halogen which is preferably fluorine. The $C_1$-$C_{10}$ alkyl group may be substituted by up to 10 halogen atoms or preferably, by up to 5 halogen atoms, i.e., 1, 2, 3, 4 or 5 halogen atoms. For example, $R_1$ may be CF$_3$, CHF$_2$, CH$_2$CF$_3$, CH$_2$CHF$_2$ or CF$_2$CF$_3$. This means that $R'$ may be CF$_3$, CHF$_2$, CH$_2$CF$_3$, CH$_2$CHF$_2$ or CF$_2$CF$_3$ or OCF$_3$, OCHF$_2$, OCH$_2$CF$_3$, OCH$_2$CHF$_2$ or OCF$_2$CF$_3$, most preferably CF$_3$.

In a preferred embodiment, R is H or $C_1$ to $C_6$ alkyl, preferably H.

Preferably in at least one, preferably both, of L, the atom that is directly bonded to X is a carbon, and at least one nitrogen atom is directly bonded to said carbon (preferably via a double bond). More preferably, said nitrogen atom is a hydrogen bond acceptor.

Preferably, in addition to a N atom, L contains at least one other heteroatom in the heteroaryl ring which is selected from N, O or S.

In a preferred embodiment, each L is independently selected from:

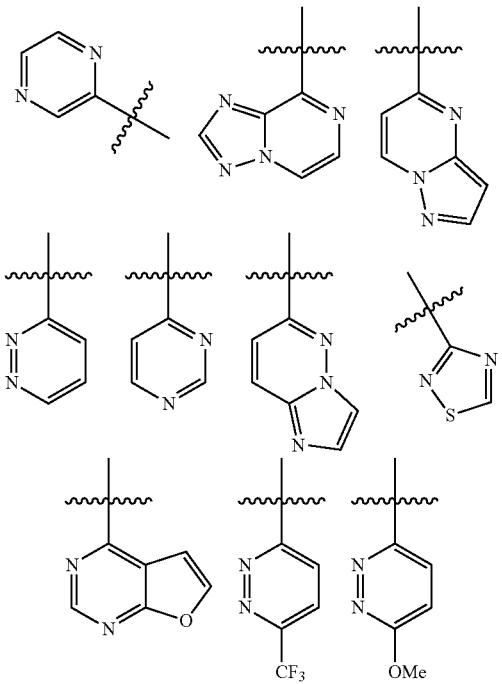

-continued

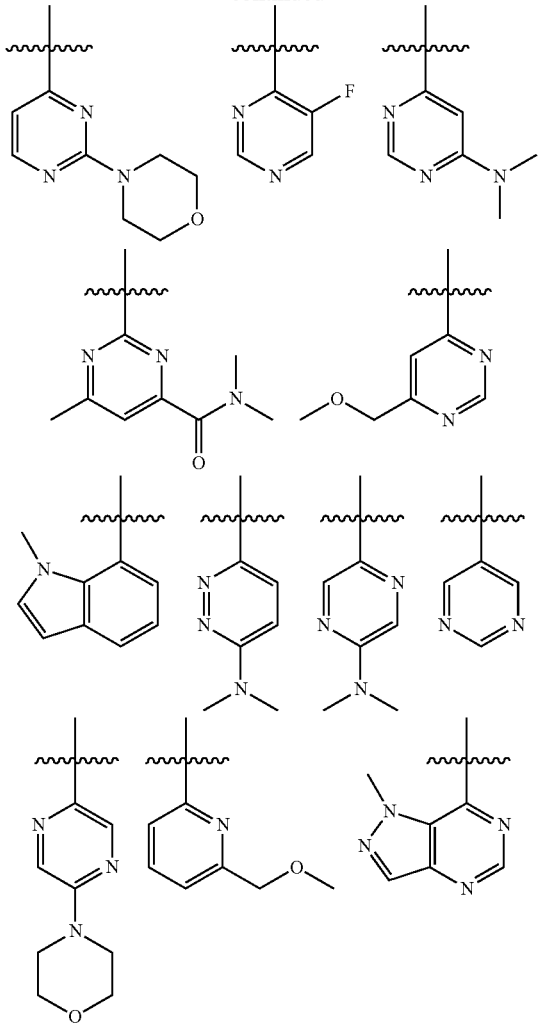

In some embodiments the invention is represented by a compound of the formula

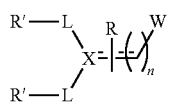

wherein:
⸺ is a double bond and X is C; or
⸺ is a single bond and X is N, CH or CQR$_1$, and
wherein:
n is 1 to 10;
R is H or QR$_1$;
each R' is independently selected from H and QR$_1$;
each Q is independently selected from a bond, CO, CO$_2$, NH, S, SO, SO$_2$ or O;
each R$_1$ is independently selected from H, C$_1$-C$_{10}$ alkyl, C$_2$-C$_{10}$ alkenyl, C$_2$-C$_{10}$ alkynyl, aryl, heteroaryl, C$_1$-C$_{10}$ cycloalkyl, halogen, C$_1$-C$_{10}$ alkylaryl, C$_1$-C$_{10}$ alkyl heteroaryl, C$_1$-C$_{10}$ heterocycloalkyl or trifluoromethyl,
L is independently a 5- to 12-membered heteroaryl, wherein each L contains at least two nitrogen atoms;
W is a zinc-binding group;
each aryl or heteroaryl may be substituted by up to five substituents selected from C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis(C$_1$-C$_3$ alkyl) amino C$_1$-C$_3$ alkyl, C$_1$-C$_3$-acylamino, C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl and bis C$_1$-C$_3$-alkyl aminosulfonyl; and
each alkyl, alkenyl or alkynyl may be optionally substituted with C$_1$-C$_{10}$ alkyl, C$_2$-C$_{10}$ alkenyl, C$_2$-C$_{10}$ alkynyl, aryl, cycloalkyl, heteroaryl, halogen, NH$_2$, NO$_2$ or hydroxyl, or a pharmaceutically acceptable salt thereof.

For the avoidance of doubt, the above embodiment can be combined with any of the preferred features described herein.

In some embodiments, the invention is a compound represented by:

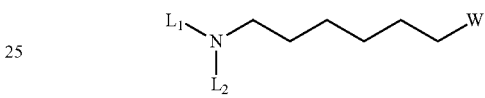

or a pharmaceutically acceptable salt thereof,
wherein
L$_1$ is a 5-6 membered monocyclic heteroaryl having at least 2 nitrogen atoms;
L$_2$ is a 5-6 membered monocyclic heteroaryl having at least 2 nitrogen atoms, or a 9-10 membered bicyclic heteroaryl having at least 2 nitrogen atoms; wherein L$_1$ and L$_2$ are each optionally substituted by one, two or three substituents each independently selected from RL;
RL is selected for each occurrence from the group consisting of: C$_{1-6}$alkyl, C$_{2-6}$alkenyl, C$_{2-6}$alkynyl; C$_{1-6}$alkoxy, C$_{3-6}$cycloalkyl, halogen, NR$^a$R$^b$; —C(O)—NR$^a$R$^b$, —NR$^a$C(O)—R$^a$, and —NR$^a$SO$_2$—R$^a$ (wherein C$_{1-6}$alkyl, C$_{2-6}$alkenyl, C$_{2-6}$ alkynyl, C$_{1-6}$alkoxy and C$_{3-6}$cycloalkyl may be optionally substituted by one, two or three halogens or C$_{1-6}$alkoxy),
R$^a$ and R$^b$ are each independently selected from H or C$_{1-4}$alkyl; or R$^a$ and R$^b$ taken together with the nitrogen to which they are attached form a 4-6 membered heterocycle; and
W is a zinc binding group.
Preferably, the compound is represented by:

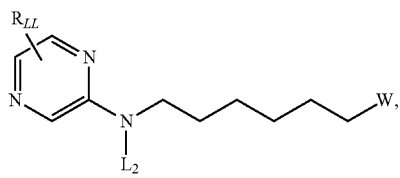

wherein R$_{LL}$ is selected for each occurrence from the group consisting of H, F, CF$_3$, and CH$_3$.

Preferably, wherein L$_2$ is a 6 membered monocyclic heteroaryl having two nitrogens.

More preferably, the compound is represented by:

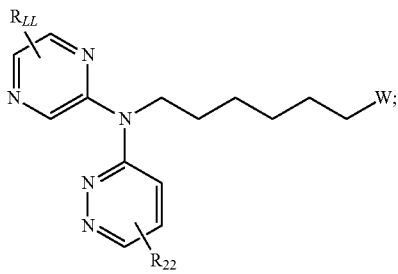

wherein $R_{22}$ is selected from the group consisting of H, F, $NR^aR^b$; $C_{1-2}$alkoxy, and methoxymethyl.

A pharmaceutical composition of the invention comprises a compound as defined above, and a pharmaceutically acceptable carrier or diluent. A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, ethanedisulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the present invention are found to be inhibitors of HDAC. The compounds of the present invention are therefore therapeutically useful in the treatment of conditions affected by HDAC activity.

The compounds of the invention may be prepared by synthetic routes that will be apparent to those skilled in the art, e.g. based on the Examples.

The compounds of the present invention are found to be inhibitors of HDAC. The compounds of the present invention are therefore therapeutically useful.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

In one embodiment the compounds of the present invention may be used in combination with another known inhibitor of HDAC, such as SAHA. In this embodiment, the combination product may be formulated such that it comprises each of the medicaments for simultaneous, separate or sequential use.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by co-administration with another chemotherapeutic or antineoplastic agent. The compound of the invention and the said other agent may be administrated in any order. In both these cases the compound of the invention and the other agent may be administered together or, if separately, in any order as determined by a physician.

HDAC is believed to contribute to the pathology and/or symptomology of several different diseases such that reduction of the activity of HDAC in a subject through inhibition of HDAC may be used to therapeutically address these disease states. Examples of various diseases that may be treated using the HDAC inhibitors of the present invention are described herein.

One set of indications that HDAC inhibitors of the present invention may be used to treat is those involving undesirable or uncontrolled cell proliferation. Such indications include benign tumours, various types of cancers such as primary tumours and tumour metastasis, restenosis (e.g. coronary, carotid, and cerebral lesions), abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants. More specific indications for HDAC inhibitors include, but are not limited to prostate cancer, lung cancer, acute leukaemia, multiple myeloma, bladder carcinoma, renal carcinoma, breast carcinoma, colorectal carcinoma, neuroblastoma and melanoma.

In one embodiment, a method is provided for treating diseases associated with undesired and uncontrolled cell proliferation. The method comprises administering to a subject suffering from uncontrolled cell proliferation a therapeutically effective amount of a HDAC inhibitor according to the present invention, such that said uncontrolled cell proliferation is reduced. The particular dosage of the inhibitor to be used will depend on the severity of the disease state, the route of administration, and related factors that can be determined by the attending physician. Generally, acceptable and effective daily doses are amounts sufficient to effectively slow or eliminate uncontrolled cell proliferation.

HDAC inhibitors according to the present invention may also be used in conjunction with other agents to inhibit undesirable and uncontrolled cell proliferation. Examples of other anti-cell proliferation agents that may be used in conjunction with the HDAC inhibitors of the present invention include, but are not limited to, retinoid acid and derivatives thereof, 2-methoxyestradiol, Angiostatin™ protein, Endostatin™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulfate (clupeine), sulfated chitin derivatives (prepared from queen crab shells), sulfated polysaccharide peptidoglycan complex (sp-pg), staurosporine, modulators of matrix metabolism, including for example, proline analogs ((1-azetidine-2-carboxylic acid (LACA), cishydroxyproline, d,l-3,4-dehydroproline, thiaproline), beta-aminopropionitrile fumarate, 4-propyl-5-(4-pyridinyl)-2(3H)-oxazolone; methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide; angiostatic steroid, carboxyaminoimidazole; metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Generally, cells in benign tumours retain their differentiated features and do not divide in a completely uncontrolled manner. A benign tumour is usually localized and nonmetastatic. Specific types of benign tumours that can be treated using HDAC inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumours, or metastases, are tumours that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumours, either primary or secondary, that can be treated using the HDAC inhibitors of the present invention include, but are not limited to, leukaemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumour, small-cell lung tumour, gallstones, islet cell tumour, primary brain tumour, acute and chronic lymphocytic and granulocytic tumours, hairy-cell tumour, adenoma, hyperplasia, medullary carcinoma, pheochromocytoma, mucosal neuromas, intestinal ganglioneuromas, hyperplastic corneal nerve tumour, marfanoid habitus tumour, Wilms' tumour, seminoma, ovarian tumour, leiomyomater tumour, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumour, polycythermia vera, adenocarcinoma, glioblastoma multiforme, leukemias, lymphomas, malignant melanomas, epidermoid carcinomas, and other carcinomas and sarcomas.

The HDAC inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the HDAC inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using HDAC inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularization and corneal neovascularization. Examples of diseases which include some component of retinal/choroidal neovascularization include, but are not limited to, Best's diseases, myopia, optic pits, Stargart's diseases, Paget's disease, vein occlusion, artery occlusion, sickle cell anemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or choroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HDAC inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a HDAC inhibitor alone or in conjunction with other anti-inflammatory agents may prevent the formation of the granulomas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HDAC inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HDAC inhibitors according to the present invention to inhibit angiogenesis, such granulomas formation can be inhibited. Psoriasis, also a chronic and recurrent inflammatory disease, is characterized by papules and plaques of various sizes.

Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HDAC inhibitors according to the present invention alone or in conjunction with other anti-RA agents may prevent the formation of new blood vessels necessary to maintain the chronic inflammation.

The compounds of the present invention can further be used in the treatment of cardiac/vasculature diseases such as hypertrophy, hypertension, myocardial infarction, reperfusion, ischaemic heart disease, angina, arrhythmias, hypercholesterolemia, atherosclerosis and stroke. The compounds can further be used to treat neurodegenerative disorders/CNS disorders such as acute and chronic neurological diseases, including stroke, Huntington's disease, Amyotrophic Lateral Sclerosis and Alzheimer's disease.

The compounds of the present invention can also be used as antimicrobial agents, for example antibacterial agents. The invention therefore also provides a compound for use in the treatment of a bacterial infection. The compounds of the present invention can be used as anti-infectious compounds against viral, bacterial, fungal and parasitic infections. Examples of infections include protozoal parasitic infections (including *plasmodium, cryptosporidium parvum, toxoplasma gondii, sarcocystis neurona* and *Eimeria* sp.)

The compounds of the present invention are particularly suitable for the treatment of undesirable or uncontrolled cell proliferation, preferably for the treatment of benign tumours/hyperplasias and malignant tumours, more preferably for the treatment of malignant tumours and most preferably for the treatment of chronic lymphocytic leukaemia (CLL), breast cancer, prostate cancer, ovarian cancer, mesothelioma, T-cell lymphoma.

In a preferred embodiment of the invention, the compounds of the invention are used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, organ transplant rejection, diabetes, osteoporosis, MDS, benign prostatic hyperplasia, oral leukoplakia, a genetically related metabolic disorder, an infection, Rubens-Taybi, fragile X syndrome, or alpha-1 antitrypsin deficiency, or to accelerate wound healing, to protect hair follicles or as an immunosuppressant.

Typically, said inflammatory condition is a skin inflammatory condition (for example psoriasis, acne and eczema), asthma, chronic obstructive pulmonary disease (COPD), rheumatoid arthritis (RA), inflammatory bowel disease (IBD), Crohn's disease or colitis.

Typically, said cancer is chronic lymphocytic leukaemia, breast cancer, prostate cancer, ovarian cancer, mesothelioma or T-cell lymphoma.

Typically, said cardiovascular disease is hypertension, myocardial infarction (MI), ischemic heart disease (IHD) (reperfusion), angina pectoris, arrhythmia, hypercholesterolemia, hyperlipidaemia, atherosclerosis, stroke, myocarditis, congestive heart failure, primary and secondary i.e. dilated (congestive) cardiomyopathy, hypertrophic cardiomyopathy, restrictive cardiomyopathy, peripheral vascular disease, tachycardia, high blood pressure or thrombosis.

Typically, said genetically related metabolic disorder is cystic fibrosis (CF), peroxisome biogenesis disorder or adrenoleukodystrophy.

Typically, the compounds of the invention are used as an immunosuppressant following organ transplant.

Typically, said infection is a viral, bacterial, fungal or parasitic infection, in particular an infection by *S. aureus*, P acne, *candida* or *aspergillus*.

Typically, said CNS disorder is Huntingdon's disease, Alzheimer's disease, multiple sclerosis or amyotrophic lateral sclerosis.

In this embodiment, the compounds of the invention may be used to alleviate cancer, cardiac hypertrophy, chronic heart failure, an inflammatory condition, a cardiovascular disease, a haemoglobinopathy, a thalassemia, a sickle cell disease, a CNS disorder, an autoimmune disease, diabetes or osteoporosis, or are used as an immunosuppressant.

The compounds of the invention may also be used to alleviate chronic lymphocytic leukaemia (CLL), breast cancer, prostate cancer, ovarian cancer, mesothelioma, T-cell lymphoma, cardiac hypertrophy, chronic heart failure or a skin inflammatory condition, in particular psoriasis, acne or eczema.

The compounds of the present invention can be used in the treatment of animals, preferably in the treatment of mammals and more preferably in the treatment of humans.

The compounds of the invention may, where appropriate, be used prophylactically to reduce the incidence of such conditions.

In use, a therapeutically effective amount of a compound of the invention is administered to a patient. A typical dose is from about 0.001 to 50 mg per kg of body weight, according to the activity of the specific compound, the age, weight and conditions of the subject to be treated, the type and severity of the disease and the frequency and route of administration.

Compounds of the invention may be tested for HDAC inhibitory activity by any suitable assay, e.g. the assay described in WO2008/062201.

The following Examples illustrate the invention.

Example A

7-[Bis(pyrazin-2-yl)amino]-N-hydroxyheptanamide

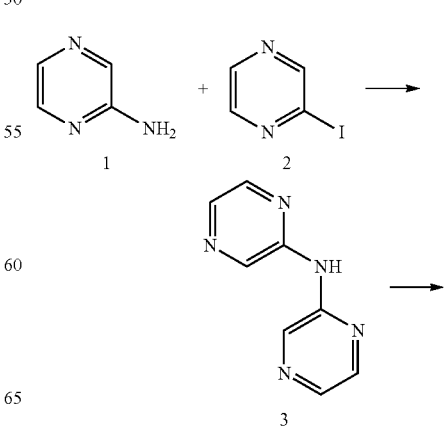

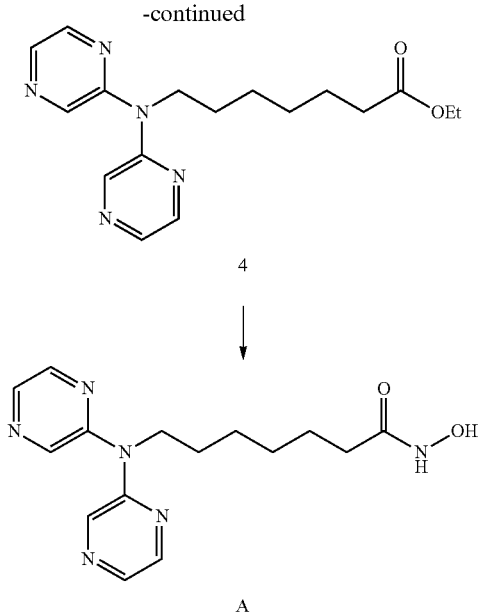

A solution of 2-iodopyrazine (2) (2.59 g, 27.2 mmol), pyrazin-2-amine (1) (5.10 g, 24.8 mmol), Cs$_2$CO$_3$ (24.2 g, 74.3 mmol) and Xantphos (573 mg, 0.99 mmol) in dioxane (100 mL) was purged with Ar(g) for 10 min. Pd$_2$(dba)$_3$ (680 mg, 0.74 mmol) was added and mixture was heated up to 90° C. overnight. Once cooled, it was partitioned between H$_2$O (200 mL) and EtOAc (3×200 mL). The combined organics were dried over MgSO$_4$, filtered and concentrated in vacuo.

ture was stirred at 70° C. under Ar(g) for 1 h. Once cooled, it was partitioned between H$_2$O (10 mL), EtOAc (3×10 mL). The combined organics were dried over MgSO$_4$, filtered and concentrated in vacuo. The resulting residue was purified by flash column chromatography with hexane/EtOAc (1:0-2:3) to yield ethyl 7-[bis(pyrazin-2-yl)amino]heptanoate (4) as a yellow solid (709 mg, 78%).

$^1$H NMR (300 MHz, Chloroform-d) δ$_H$ ppm: 8.59 (d, J=1.3 Hz, 2H), 8.25-8.32 (m, 2H), 8.16 (d, J=2.4 Hz, 2H), 4.07-4.22 (m, 4H), 2.28 (t, J=7.4 Hz, 2H), 1.68-1.81 (m, 2H), 1.62 (quin, J=7.3 Hz, 2H), 1.32-1.46 (m, 4H), 1.25 (t, J=7.2 Hz, 3H). LCMS (ES): Found 330.2 [M+H]$^+$.

To a solution of (4) (709 mg, 2.15 mmol) in MeOH/THF (1:1, 20 mL) was added hydroxylamine (50% w/w in H$_2$O; 2.84 mL, 43.0 mmol) followed by 6N NaOH (0.72 mL, 4.3 mmol). The mixture was stirred at rt for 1 h. Then, it was quenched with 1M KHSO$_4$ (30 mL) and partitioned between H$_2$O (20 mL) and CH$_2$Cl$_2$ (3×50 mL). The combined organics were dried over MgSO$_4$, filtered and concentrated in vacuo to yield 7-[bis(pyrazin-2-yl)amino]-N-hydroxyheptanamide (A) as a white solid (378 mg, 56%).

$^1$H NMR (300 MHz, DMSO-d$_6$) δ$_H$ ppm: 10.30 (br. s., 1H), 8.59-8.67 (m, 3H), 8.33 (dd, J=2.4, 1.5 Hz, 2H), 8.21 (d, J=2.6 Hz, 2H), 4.07-4.17 (m, 2H), 1.91 (t, J=7.3 Hz, 2H), 1.54-1.69 (m, 2H), 1.44 (quin, J=7.2 Hz, 2H), 1.16-1.36 (m, 4H). LCMS (ES): Found 317.2 [M+H]$^+$.

Example B

N-Hydroxy-7-[(pyrazin-2-yl)({[1,2,4]triazolo[1,5-a]pyrazin-8-yl}amino]heptanamide

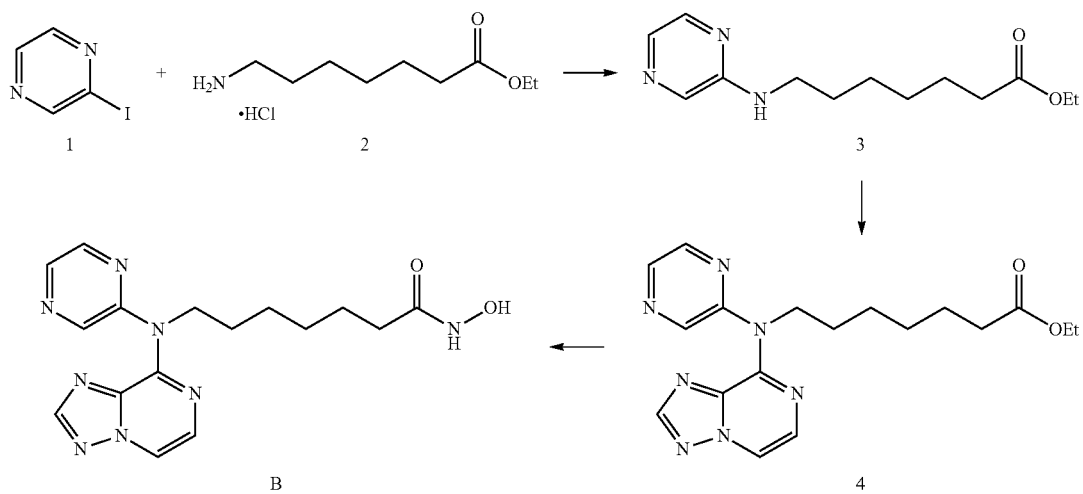

The resulting residue was purified by flash column chromatography with hexane/EtOAc (4:1-0:1) then EtOAc/MeOH (1:0-3:1) to yield (3) as an off white solid (2.58 g, 60%).

$^1$H NMR (300 MHz, Chloroform-d) δ$_H$ ppm: 8.99 (d, J=1.4 Hz, 2H), 8.30 (dd, J=2.6, 1.5 Hz, 2H), 8.11 (d, J=2.7 Hz, 2H).

LCMS (ES): Found 174.1 [M+H]$^+$.

NaH (60%) (121 mg, 3.0 mmol) was added portion-wise to N-(pyrazin-2-yl)pyrazin-2-amine (3) (475 mg, 2.74 mmol) in DMF (10 mL) at 0° C. under Ar(g). The reaction mixture was then stirred for 20 min and ethyl-7-iodoheptanoate (857 mg, 3.0 mmol) was added. The reaction mix- To a flask were added 2-iodopyrazine (1) (10 g, 48.5 mmol), ethyl 7-aminoheptanoate hydrochloride (2) (13.2 g, 63.1 mmol), Cs$_2$CO$_3$ (47.5 g, 145.5 mmol) and CuI (0.461 g, 2.42 mmol) under Ar(g). DMF (100 mL) was then added followed by 2-isobutyrylcyclohexanone (1.62 mL, 9.7 mmol). The reaction mixture was then left to stir overnight at rt under Ar(g). The mixture was partitioned between H$_2$O (10 mL) and EtOAc (3×50 mL). The combined organics were washed with brine (2×25 mL), dried over MgSO$_4$, filtered and concentrated in vacuo. The residue was purified by flash column chromatography with hexane/EtOAc (7:3-

3:7) to yield ethyl-7-[(pyrazin-2-yl)amino]heptanoate (3) as a brown solid (11.25 g, 93%).

$^1$H NMR (300 MHz, Chloroform-d) $\delta_H$ ppm: 7.44-9.08 (m, 3H), 5.00 (br. s., 1H), 4.13 (q, J=7.1 Hz, 2H), 3.35 (t, J=6.8 Hz, 2H), 2.31 (t, J=7.4 Hz, 2H), 1.59-1.72 (m, 4H), 1.33-1.50 (m, 4H), 1.26 (t, J=7.2 Hz, 3H).

LCMS (ES): Found 252.0 [M+H]$^+$.

A solution of (3) (100 mg, 0.40 mmol), 8-chloro-[1,2,4]triazolo[1,5-a]pyrazine (74.2 mg, 0.48 mmol), Cs$_2$CO$_3$ (390 mg, 1.20 mmol) and BINAP (15 mg, 0.02 mmol) in dioxane (4 mL) was purged with Ar(g) for 10 min. Pd$_2$(dba)$_3$ (11 mg, 0.012 mmol) was added and mixture was heated up to 90° C. overnight. Once cooled, it was partitioned between H$_2$O (10 mL) and EtOAc (3×10 mL). The combined organics were dried over MgSO$_4$, filtered and concentrated in vacuo. The resulting residue was purified by flash column chromatography to yield (4) as an off white solid (110 mg, 75%).

$^1$H NMR (300 MHz, Chloroform-d) $\delta_H$ ppm: 8.43 (d, J=0.8 Hz, 1H), 8.34 (dd, J=2.5, 1.4 Hz, 1H), 8.27 (d, J=2.4 Hz, 1H), 8.16-8.23 (m, 2H), 7.74-7.81 (m, 1H), 4.43 (dd, J=8.3, 7.0 Hz, 2H), 4.03-4.16 (m, 2H), 2.19-2.31 (m, 2H), 1.77 (quin, J=7.4 Hz, 2H), 1.59 (quin, J=7.3 Hz, 2H), 1.28-1.46 (m, 4H), 1.18-1.27 (m, 3H). LCMS (ES): Found 370.2 [M+H]$^+$.

To a solution of (4) (110 mg, 0.30 mmol) in MeOH/THF (1:1, 5 mL) was added hydroxylamine (50% w/w in H$_2$O; 0.60 mL, 6 mmol) followed by NaOH (95 mg, 2.38 mmol). The mixture was stirred at rt for 10 min. Then, it was concentrated in vacuo and purified by reverse phase column chromatography with H$_2$O/MeCN (19:1-1:1) to yield N-hydroxy-7-[(pyrazin-2-0({[1,2,4]triazolo[1,5-a]pyrazin-8-yl})amino]heptanamide (B) as a white solid (24.6 mg, 23%).

$^1$H NMR (300 MHz, DMSO-d$_6$) $\delta_H$ ppm: 8.59-8.72 (m, 1H), 8.53 (d, J=1.5 Hz, 1H), 8.43-8.50 (m, 1H), 8.40 (dd, J=2.5, 1.4 Hz, 1H), 8.23-8.35 (m, 1H), 7.91 (d, J=4.5 Hz, 1H), 4.20-4.48 (m, 2H), 1.85 (t, J=7.3 Hz, 2H), 1.55-1.78 (m, 2H), 1.41 (quin, J=7.2 Hz, 2H), 1.11-1.35 (m, 4H).

LCMS (ES): Found 357.2 [M+H]$^+$.

Example C

N-Hydroxy-7-[(pyrazin-2-yl)({pyrazolo[1,5-a]pyrimidin-5-yl})amino]heptanamide

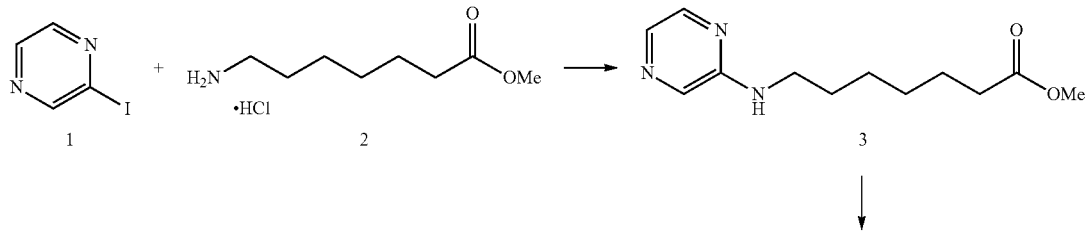

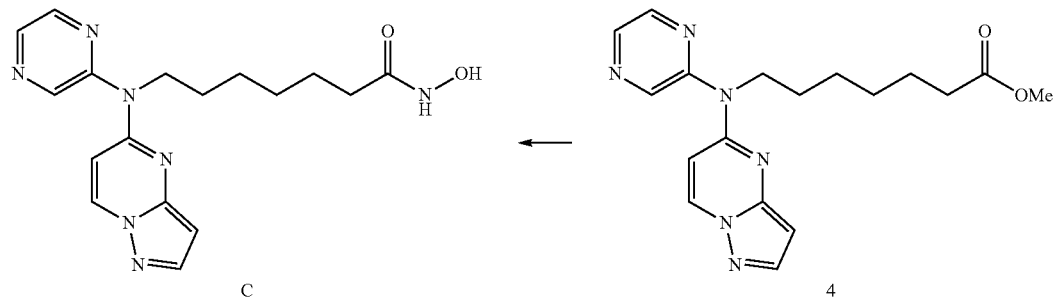

To a flask were added 2-iodopyrazine (1) (3.5 g, 17.0 mmol), methyl 7-aminoheptanoate hydrochloride (2) (4.3 g, 22.1 mmol), Cs$_2$CO$_3$ (16.6 g, 51.0 mmol) and CuI (0.16 g, 0.85 mmol) under Ar(g). DMF (35 mL) was then added followed by 2-isobutyrylcyclohexanone (0.57 mL, 3.40 mmol). The reaction mixture was then left to stir overnight at rt under Ar(g). The mixture was partitioned between H$_2$O (200 mL) and EtOAc (3×150 mL). The combined organics were washed with brine (2×50 mL), dried over MgSO$_4$, Hz, 1H), 6.31 (dd, J=2.2, 0.7 Hz, 1H), 4.07-4.20 (m, 2H), 1.91 (t, J=7.4 Hz, 2H), 1.64 (quin J=7.4 Hz, 2H), 1.45 (quin J=7.4 Hz, 2H), 1.18-1.35 (m, 4H).

LCMS (ES): Found 356.4 [M+H]$^+$.

Example D

N-Hydroxy-7-[(pyrazin-2-yl)[6-(trifluoromethyl)pyridazin-3-yl]amino]heptanamide

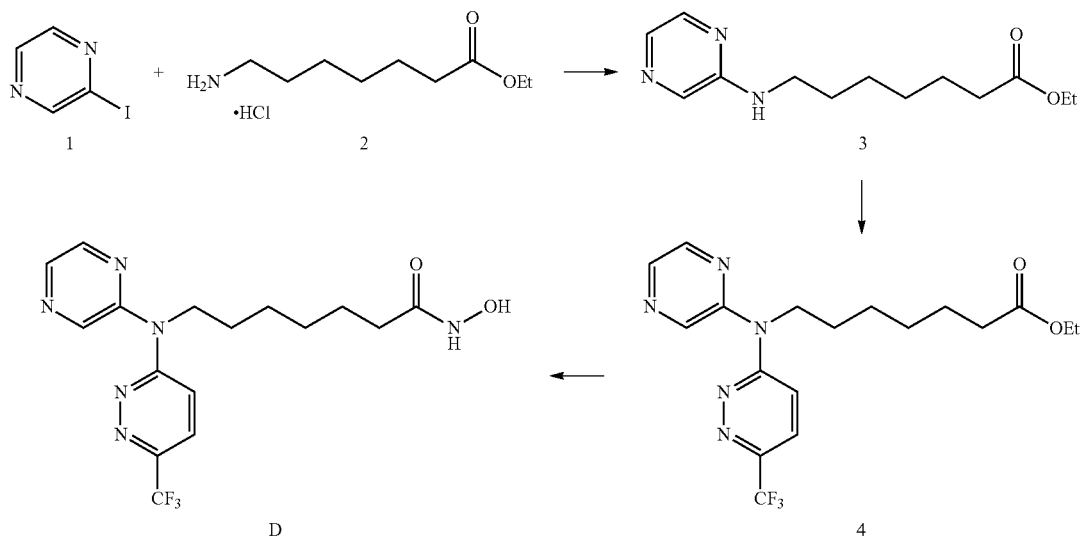

filtered and concentrated in vacuo. The residue was purified by flash column chromatography with hexane/EtOAc (9:1-3:7) to yield methyl-7-[(pyrazin-2-yl)amino]heptanoate (3) as a brown solid (3.11 g, 77%).

$^1$H NMR (300 MHz, Chloroform-d) δ$_H$ ppm: 7.97 (dd, J=2.7, 1.4 Hz, 1H), 7.92 (d, J=1.3 Hz, 1H), 7.80 (d, J=2.8 Hz, 1H), 4.84 (br. s., 1H), 3.68 (s, 3H), 3.29-3.42 (m, 2H), 2.33 (t, J=7.4 Hz, 2H), 1.66 (quin, J=7.0 Hz, 4H), 1.34-1.51 (m, 4H). LCMS (ES): Found 238.0 [M+H]$^+$.

A solution of (3) (125 mg, 0.53 mmol), 5-bromopyrazolo[1,5-a]pyrimidine (0.81 mL, 0.63 mmol), Cs$_2$CO$_3$ (343 mg, 1.05 mmol) and Xantphos (15 mg, 0.03 mmol) in dioxane (3 mL) was purged with Ar(g) for 10 min. Pd$_2$(dba)$_3$ (12 mg, 0.01 mmol) was added and mixture was heated up to 90° C. overnight. Once cooled, it was partitioned between H$_2$O (10 mL) and CH$_2$Cl$_2$ (3×10 mL). The combined organics were dried over MgSO$_4$, filtered and concentrated in vacuo. The resulting residue was purified by flash column chromatography with heptane/EtOAc (1:0-0:1) then EtOAc/MeOH (1:0-4:1) to yield (4) as a yellow residue (109 mg, 48%).

LCMS (ES): Found 355.4 [M+H]$^+$.

To a solution of (4) (109 mg, 0.26 mmol) in MeOH/THF (1:1, 2 mL) was added hydroxylamine (50% w/w in H$_2$O; 0.34 mL, 5.5 mmol) followed by 6N NaOH (0.92 mL, 0.56 mmol). The mixture was stirred at rt for 15 min. Then, it was quenched with 1M KHSO$_4$ (2 mL) followed by H$_2$O (5 mL) which resulted in a suspension. The solids were filtered, washed with MeCN (1 mL) and dried in vacuo to yield N-hydroxy-7-[(pyrazin-2-yl)({pyrazolo[1,5-a]pyrimidin-5-yl})amino]heptanamide (C) as a white solid (88 mg, 81%).

$^1$H NMR (500 MHz, DMSO-d$_6$) δ$_H$ ppm: 10.30 (s, 1H), 8.69-8.84 (m, 2H), 8.63 (s, 1H), 8.47 (dd, J=2.6, 1.5 Hz, 1H), 8.35 (d, J=2.6 Hz, 1H), 8.00 (d, J=2.2 Hz, 1H), 6.74 (d, J=7.7

A solution of (3) (5.0 g, 20 mmol), 3-bromo-6-(trifluoromethyl)pyridazine (5.42 g, 23.9 mmol), Cs$_2$CO$_3$ (20.0 g, 60 mmol) and BINAP (1.24 g, 2.0 mmol) in dioxane (100 mL) was purged with Ar(g) for 10 min. Pd$_2$(dba)$_3$ (915 mg, 1.0 mmol) was added and mixture was heated up to 100° C. overnight. Once cooled, it was partitioned between H$_2$O (50 mL) and EtOAc (3×100 mL). The combined organics were dried over MgSO$_4$, filtered and concentrated in vacuo. The resulting residue was purified by flash column chromatography with hexane/EtOAc (1:0-1:3) to yield (4) as a brown oil (7.95 g, 75%).

$^1$H NMR (300 MHz, Chloroform-d) δ$_H$ ppm: 8.65 (br. s., 1H), 8.29-8.43 (m, 2H), 7.46-7.63 (m, 2H), 4.29-4.41 (m, 2H), 4.12 (q, J=7.2 Hz, 2H), 2.28 (t, J=7.3 Hz, 2H), 1.73-1.93 (m, 2H), 1.62 (quin, J=7.3 Hz, 2H), 1.32-1.50 (m, 4H), 1.22-1.30 (m, 3H).

LCMS (ES): Found 398.2 [M+H]$^+$.

To a solution of (4) (1.23 g, 3.10 mmol) in MeOH/THF (1:1, 40 mL) was added hydroxylamine (50% w/w in H$_2$O; 1.03 mL, 62 mmol) followed by 6N NaOH (1.03 mL, 6.2 mmol). The mixture was stirred at rt for 1 h. Then, it was quenched with 1M KHSO$_4$ (30 mL) and partitioned between H$_2$O (30 mL) and CH$_2$Cl$_2$ (3×50 mL). The combined organics were dried over MgSO$_4$, filtered, concentrated in vacuo and purified by C$_{18}$ reverse phase column chromatography with H$_2$O/MeCN (19:1-1:1) to yield N-hydroxy-7-[(pyrazin-2-yl)[6-(trifluoromethyl)pyridazin-3-yl]amino]heptanamide (D) as an orange gum (994 mg, 83%).

$^1$H NMR (300 MHz, DMSO-d$_6$) δ$_H$ ppm: 8.92-10.19 (m, 2H), 8.81 (d, J=1.3 Hz, 1H), 8.46 (dd, J=2.5, 1.4 Hz, 1H), 8.40 (d, J=2.4 Hz, 1H), 7.96 (d, J=9.4 Hz, 1H), 7.72 (d, J=9.4 Hz, 1H), 4.16-4.31 (m, 2H), 1.90 (t, J=7.3 Hz, 2H), 1.58-1.74 (m, 2H), 1.45 (quin, J=7.2 Hz, 2H), 1.17-1.38 (m, 4H).

LCMS (ES): Found 385.2 [M+H]$^+$.

Example E

N-Hydroxy-7-[(6-methoxypyridazin-3-yl)(pyrazin-2-yl)amino]heptanamide

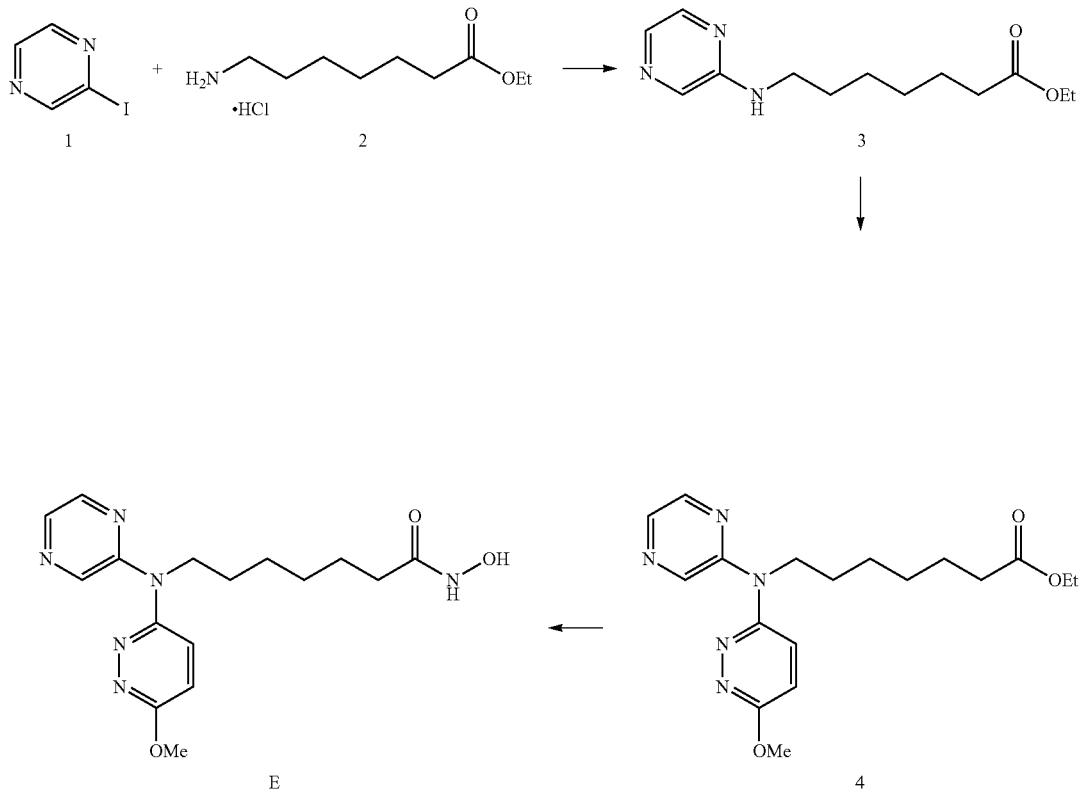

A solution of (3) (3.0 g, 11.9 mmol), 3-chloro-6-methoxypyridazine (2.07 g, 14.3 mmol), $Cs_2CO_3$ (11.6 g, 35.7 mmol) in dioxane (100 mL) was purged with Ar(g) for 10 min. Xantphos (0.69 g, 1.2 mmol) and $Pd_2(dba)_3$ (550 mg, 0.6 mmol) were added and mixture was heated up to 100° C. overnight. The mixture was re-treated with $Cs_2CO_3$ (3.9 g, 11.9 mmol), 3-chloro-6-methoxypyridazine (0.86 g, 7.2 mmol), Xantphos (0.69 g, 1.2 mmol) and $Pd_2(dba)_3$ (550 mg, 0.6 mmol) and heated up to 100° C. overnight. Once cooled, it was partitioned between $H_2O$ (100 mL) and EtOAc (3×150 mL). The combined organics were dried over $MgSO_4$, filtered and concentrated in vacuo. The resulting residue was purified by flash column chromatography with hexane/EtOAc (1:0-3:7) to yield (4) (3.8 g, ~53% pure).

To a solution of impure (4) (3.69 g, 10.27 mmol) in MeOH/THF (1:1, 140 mL) was added hydroxylamine (50% w/w in $H_2O$; 12.6 mL, 205 mmol) followed by 6N NaOH (6.8 mL, 41.1 mmol). The mixture was stirred at rt for 0.5 h. Then, it was quenched with 1M $KHSO_4$ (37 mL) and partitioned between $H_2O$ (120 mL) and $CH_2Cl_2$ (3×250 mL). The combined organics were dried over $MgSO_4$, filtered and concentrated in vacuo and purified by $C_{18}$ reverse phase column chromatography with $H_2O$/MeCN (19:1-1:1) to yield N-hydroxy-7-[(6-methoxypyridazin-3-yl)(pyrazin-2-yl)amino]heptanamide (E) as pale yellow gum (1.40 g, 34% over 2 steps).

$^1$H NMR (300 MHz, DMSO-$d_6$) $\delta_H$ ppm: 9.01-9.96 (m, 2H), 8.38 (d, J=1.3 Hz, 1H), 8.22 (dd, J=2.5, 1.4 Hz, 1H), 8.08 (d, J=2.6 Hz, 1H), 7.66 (d, J=9.4 Hz, 1H), 7.20 (d, J=9.4 Hz, 1H), 4.04-4.11 (m, 2H), 4.01 (s, 3H), 1.90 (t, J=7.3 Hz, 2H), 1.53-1.69 (m, 2H), 1.45 (quin, J=7.1 Hz, 2H), 1.18-1.33 (m, 4H).

LCMS (ES): Found 347.2 [M+H]$^+$.

Example F

N-Hydroxy-7-({imidazo[1,2-b]pyridazin-6-yl}(pyrazin-2-yl)amino) heptanamide

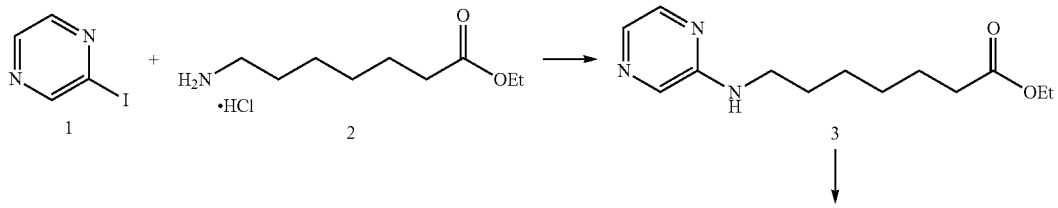

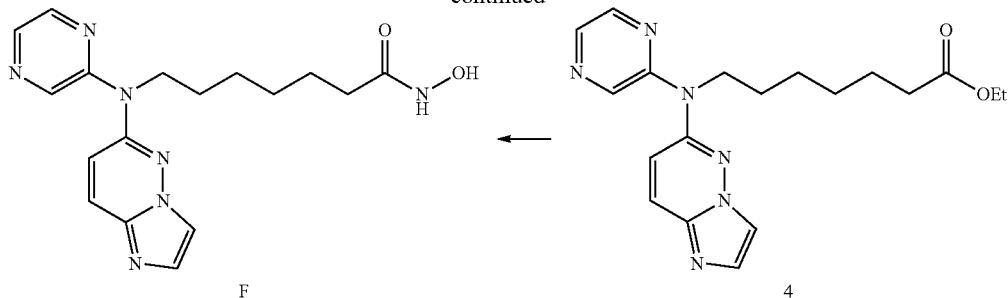

A solution of (3) (100 mg, 0.40 mmol), 6-chloroimidazo[1,2-b]pyridazine (73 mg, 0.48 mmol), $Cs_2CO_3$ (389 mg, 1.2 mmol) and BINAP (15 mg, 0.02 mmol) in dioxane (2.5 mL) was degassed with $N_2$(g) for 10 min. $Pd_2(dba)_3$ (11 mg, 0.012 mmol) was added and mixture was heated up to 90° C. overnight. Once cooled, it was partitioned between $H_2O$ (10 mL) and EtOAc (3×10 mL). The combined organics were dried over $MgSO_4$, filtered and concentrated in vacuo. The resulting residue was purified by flash column chromatography eluting with heptane/EtOAc (1:0-0:1) to yield (4) as a tan oil (76 mg, 52%).

LCMS (ES): Found 369.0 [M+H]+.

To a solution of (4) (76 mg, 0.21 mmol) in MeOH/THF (1:1, 1 mL) was added hydroxylamine (50% w/w in $H_2O$; 0.25 mL, 4.1 mmol) followed by 6N NaOH (0.07 mL, 0.41 mmol). The mixture was stirred at rt for 15 mins. Then, it was quenched with the addition of 1M $KHSO_4$ (3 mL) and $H_2O$ (5 mL), filtered and extracted with $CH_2Cl_2$ (2×10 mL). Purification by $C_{18}$ reverse phase chromatography eluting with $H_2O$/MeCN gave N-hydroxy-7-({imidazo[1,2-b]pyridazin-6-yl}(pyrazin-2-yl)amino)heptanamide (F) as pale yellow gum (21 mg, 28%).

LCMS (ES): Found 356.0 [M+H]+.

Example G

N-Hydroxy-7-[(3-methyl-1,2,4-thiadiazol-5-yl)[2-(morpholin-4-yl)pyrimidin-4-yl]amino]heptanamide

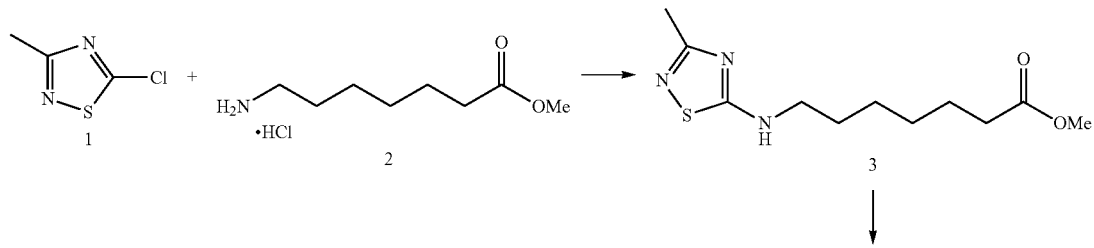

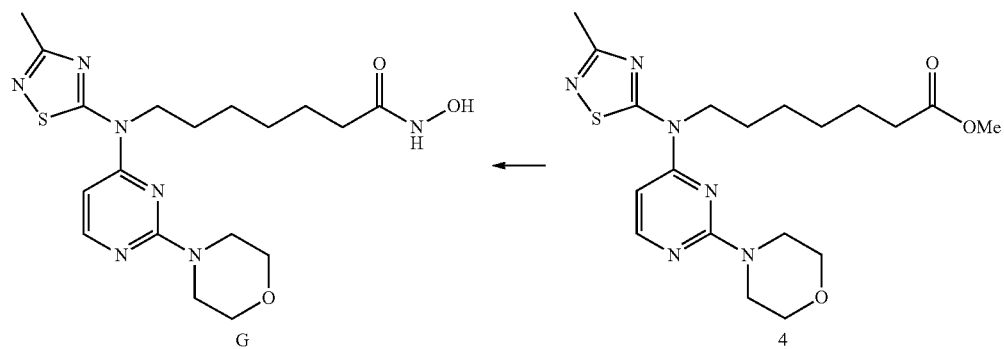

To a solution of (1) (1.64 g, 12 mmol) and (2) (2.34 g, 12 mmol) in DMF (10 mL) was added triethylamine (5 mL, 36 mmol). After 12 h stirring at rt, H$_2$O (50 mL) was added and the mixture was extracted with EtOAc (3×100 mL). The combined organics were dried over MgSO$_4$ and concentrated in vacuo. The resulting residue was purified by flash column chromatography with hexane/EtOAc (1:0-1:1) to yield (3) as a low melting solid (1.46 g, 47%).

$^1$H NMR (300 MHz, Chloroform-d) δ$_H$ ppm: 6.48-6.73 (m, 1H), 3.68 (s, 3H), 3.25 (t, J=7.3 Hz, 2H), 2.44 (s, 3H), 2.33 (t, J=7.3 Hz, 2H), 1.55-1.79 (m, 4H), 1.29-1.50 (m, 4H).

LCMS (ES): Found 258.0 [M+H]$^+$.

A solution of (3) (120 mg, 0.47 mmol), 4-(4-bromopyrimidin-2-yl)morpholine (137 mg, 0.56 mmol), Cs$_2$CO$_3$ (304 mg, 0.93 mmol) and Xantphos (13 mg, 0.02 mmol) in dry dioxane (5 mL) was degassed with N$_2$(g) for 10 min. Pd$_2$(dba)$_3$ (9 mg, 0.01 mmol) was added and the mixture was heated up to 90° C. overnight. Once cooled, it was partitioned between H$_2$O (5 mL) and EtOAc (2×15 mL). The combined organics were dried over MgSO$_4$, filtered and concentrated in vacuo. The resulting residue was purified by flash column chromatography eluting with EtOAc/Hex (0:1-1:0) to yield (4) as a yellow solid (167 mg, 78%).

LCMS (ES): Found 421.5 [M+H]$^+$.

To a solution of (4) (166 mg, 0.39 mmol) in MeOH/THF (1:1, 2 mL) was added hydroxylamine (50% w/w in H$_2$O; 0.48 mL, 7.9 mmol) followed by 6N NaOH (0.13 mL, 0.79 mmol). The mixture was stirred at rt for 15 min. The reaction was quenched with the addition of 1M KHSO$_4$ (2.5 mL) and H$_2$O (5 mL). The resulting suspension was stirred for 10 min and sonicated before the solid was collected by filtration, washing the cake with H$_2$O (2×5 mL) to give N-hydroxy-7-[(3-methyl-1,2,4-thiadiazol-5-yl)[2-(morpholin-4l1)pyrimidin-4-yl]amino]heptanamide (G) as an off-white solid (141 mg, 83%).

1H NMR (300 MHz, DMSO-d$_6$) δ$_H$ ppm: 10.32 (s, 1H), 8.64 (s, 1H), 8.32 (d, J=5.7 Hz, 1H), 6.67 (d, J=5.8 Hz, 1H), 4.30 (dd, J=8.1, 7.2 Hz, 2H), 3.76-3.91 (m, 4H), 3.65-3.77 (m, 4H), 2.44 (s, 3H), 1.94 (t, J=7.3 Hz, 2H), 1.57-1.71 (m, 2H), 1.42-1.54 (m, 2H), 1.20-1.41 (m, 4H).

LCMS (ES): Found 422.5 [M+H]$^+$.

Example H

7-[(5-Fluoropyrimidin-4-yl)(pyrazin-2-yl)amino]-N-hydroxyheptanamide

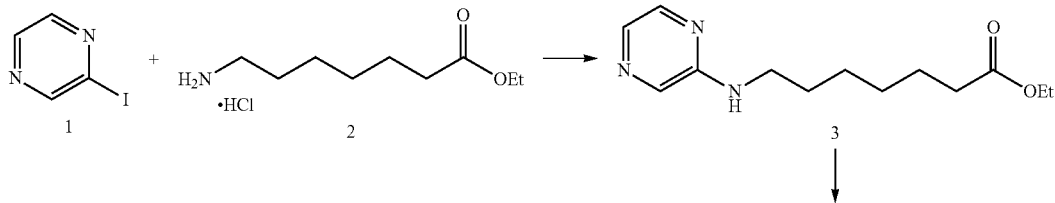

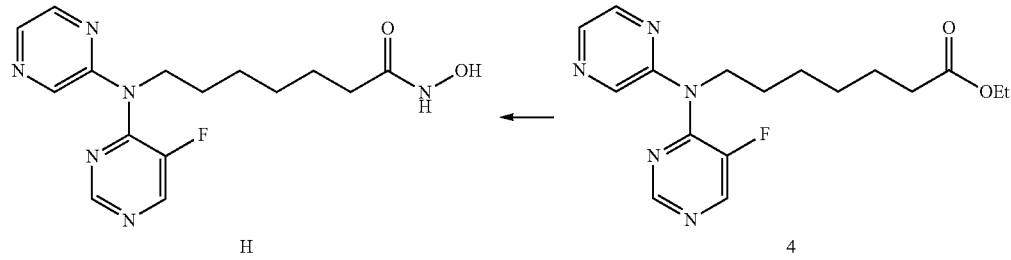

A solution of (3) (1.0 g, 4.0 mmol), 4-bromo-5-fluoropyrimidine (0.85 g, 4.8 mmol), Cs$_2$CO$_3$ (3.89 g, 11.9 mmol), BINAP (0.25 g, 0.4 mmol) and Pd$_2$(dba)$_3$ (182 mg, 0.2 mmol) in dioxane (30 mL) was purged with Ar(g) for 10 min. The mixture was then heated up to 100° C. overnight. Re-treatment was carried out with 4-bromo-5-fluoropyrimidine (0.84 g, 4.8 mmol), Cs$_2$CO$_3$ (3.89 g, 11.9 mmol), BINAP (0.25 g, 0.4 mmol) and Pd$_2$(dba)$_3$ (182 mg, 0.2 mmol) and the mixture was heated up again to 100° C. overnight. Once cooled, it was partitioned between H$_2$O (50 mL) and EtOAc (3×50 mL). The combined organics were dried over MgSO$_4$, filtered and concentrated in vacuo. The resulting residue was purified by flash column chromatography with hexane/EtOAc (1:0-0:1) to yield (4) as a pale yellow oil (0.63 g, 46%).

$^1$H NMR (300 MHz, Chloroform-d) δ$_H$ ppm: 8.71 (d, J=2.4 Hz, 1H), 8.41 (d, J=1.3 Hz, 1H), 8.28-8.37 (m, 3H), 4.17-4.25 (m, 2H), 4.12 (q, J=7.2 Hz, 2H), 2.28 (t, J=7.4 Hz, 2H), 1.68-1.80 (m, 2H), 1.62 (quin, J=7.3 Hz, 2H), 1.31-1.44 (m, 4H), 1.25 (t, J=7.2 Hz, 3H).

LCMS (ES): Found 348.2 [M+H]$^+$.

To a solution of (4) (0.63 g, 1.81 mmol) in MeOH/THF (1:1, 20 mL) was added hydroxylamine (50% w/w in H$_2$O; 2.22 mL, 36 mmol) followed by 6N NaOH (0.60 mL, 3.6 mmol). The mixture was stirred at rt for 1 h. Then, it was quenched with 1M KHSO$_4$ (20 mL) and partitioned between H$_2$O (10 mL) and CH$_2$Cl$_2$ (3×50 mL). The combined organics were dried over MgSO$_4$, filtered and concentrated in vacuo to yield 7-[(5-fluoropyrimidin-4-yl)(pyrazin-2-yl)amino]-N-hydroxyheptanamide (H) as pale yellow gum (0.56 g, 93%).

$^1$H NMR (300 MHz, DMSO-d$_6$) δ$_H$ ppm: 10.30 (s, 1H), 8.74 (d, J=2.8 Hz, 1H), 8.63 (s, 2H), 8.57 (d, J=4.9 Hz, 1H), 8.34-8.41 (m, 2H), 4.10-4.20 (m, 2H), 1.90 (t, J=7.3 Hz, 2H), 1.55-1.70 (m, 2H), 1.44 (quin, J=7.1 Hz, 2H), 1.17-1.34 (m, 4H).

LCMS (ES): Found 335.2 [M+H]$^+$.

Example I

7-{[6-(Dimethylamino)pyrimidin-4-yl](pyrazin-2-yl)amino}-N-hydroxyheptanamide

A solution of (3) (100 mg, 0.4 mmol), 6-chloro-N,N-dimethylpyrimidin-4-amine (75 mg, 0.48 mmol), Cs$_2$CO$_3$ (389 mg, 1.2 mmol) and BINAP (15 mg, 0.02 mmol) in dioxane (3 mL) was purged with N$_2$(g) for 2 min before Pd$_2$(dba)$_3$ (11 mg, 0.01 mmol) was added and the reaction heated up to 90° C. overnight. The reaction was cooled to rt and re-treatment was carried out, adding Xantphos (4 mg, 0.01 mmol) and Pd(OAc)$_2$ (4 mg, 0.02 mmol). The system was purged with N$_2$(g) and heated up to 100° C. overnight. The reaction was cooled to rt and re-treatment was carried out again, adding Xantphos (6 mg, 0.01 mmol) and Pd(OAc)$_2$ (3 mg, 0.01 mmol). The system was purged with N$_2$(g) and heated up to 100° C. overnight. The reaction mixture was cooled to rt and diluted with dioxane (3 mL), filtered through celite, washed with dioxane (3×3 mL). The filtrate was concentrated in vacuo. The resulting residue was purified by flash column chromatography with first heptane/EtOAc (1:0-0:1) then CH$_2$Cl$_2$/MeOH (1:0-9:1) to yield (4) as an orange oil (81 mg, 45%).

LCMS (ES): Found 373.2 [M+H]$^+$.

To a solution of (4) (81 mg, 0.22 mmol) in MeOH/THF (1:1, 1 mL) was added hydroxylamine (50% w/w in H$_2$O; 0.13 mL, 4.4 mmol) followed by 6N NaOH (0.07 mL, 3.6 mmol). The mixture was stirred at rt for 15 min. Then, it was quenched with 1M KHSO$_4$ (2 mL) followed by NaHCO$_3$ (sat. aq. 5 mL) and extracted with 1:2 IPA/CHCl$_3$ (4×30 mL). The combined organics were dried over MgSO$_4$, filtered and concentrated in vacuo. The resulting residue was purified by C$_{18}$ reverse phase chromatography with H$_2$O/MeCN to give 7-{[6-(dimethylamino)pyrimidin-4-yl](pyrazin-2-yl)amino}-N-hydroxyheptanamide (I) as an orange glass (28 mg, 35%).

LCMS (ES): Found 360.2 [M+H]$^+$.

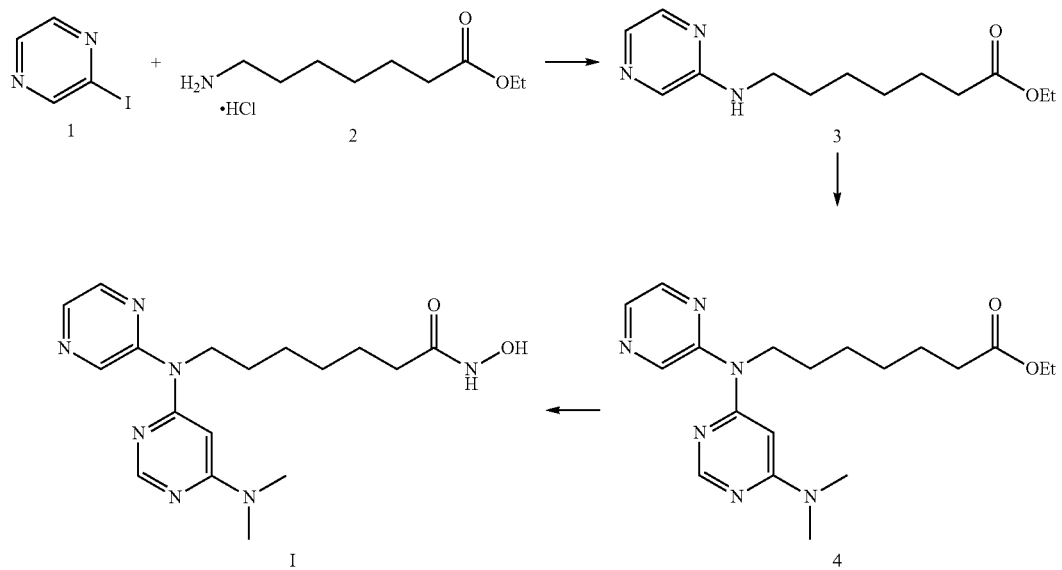

Example J

7-({Furo[2,3-d]pyrimidin-4-yl}(pyrazin-2-yl)amino)-N-hydroxyheptanamide

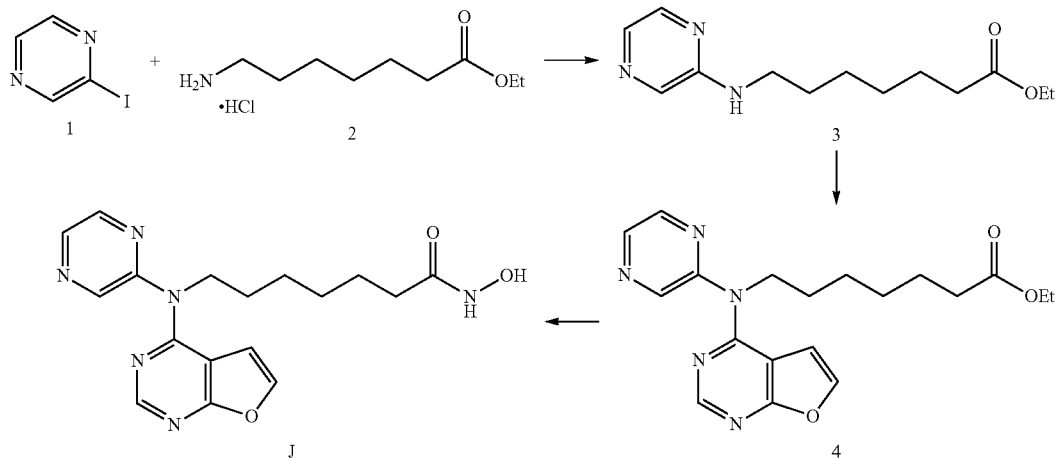

A solution of (3) (100 mg, 0.4 mmol), 4-chlorofuro[2,3-d]pyrimidine (74 mg, 0.48 mmol), $Cs_2CO_3$ (389 mg, 1.2 mmol) and BINAP (15 mg, 0.02 mmol) in dioxane (3 mL) was purged with $N_2(g)$ for 2 min before $Pd_2(dba)_3$ (11 mg, 0.01 mmol) was added and the reaction was heated up to 90° C. overnight. The reaction was cooled to rt and re-treatment was carried out, adding Xantphos (4 mg, 0.01 mmol) and $Pd(OAc)_2$ (4 mg, 0.02 mmol). The system was purged with $N_2(g)$ and heated up to 100° C. overnight. The reaction was cooled to rt and diluted with dioxane (3 mL), filtered through celite and washed with dioxane (3×3 mL). The filtrate was concentrated in vacuo. The resulting residue was purified by flash column chromatography with heptane/EtOAc (1:0-0:1) to yield (4) as an orange oil (171 mg, 94%).

LCMS (ES): Found 370.4 $[M+H]^+$.

To a solution of (4) (171 mg, 0.46 mmol) in MeOH/THF (1:1, 2 mL) was added hydroxylamine (50% w/w in $H_2O$; 0.28 mL, 9.3 mmol) followed by 6N NaOH (0.15 mL, 0.9 mmol). The mixture was stirred at rt for 15 min. Then, it was quenched with 1M $KHSO_4$ (2 mL) followed by $H_2O$ (5 mL) and extracted with $CH_2Cl_2$ (3×10 mL). The combined organics were dried over $MgSO_4$, filtered and concentrated in vacuo. The resulting residue was purified by $C_{18}$ reverse phase column chromatography eluting with $H_2O$/MeCN gave 7-({furo[2,3-d]pyrimidin-4-yl}(pyrazin-2-yl)amino)-N-hydroxyheptanamide (J) as an orange gum (57 mg, 34%).

1H NMR (300 MHz, DMSO-$d_6$) $\delta_H$ ppm: 10.30 (s, 1H), 8.74 (d, J=1.5 Hz, 1H), 8.63 (s, 1H), 8.53-8.58 (m, 2H), 8.50 (d, J=2.6 Hz, 1H), 7.87 (d, J=2.4 Hz, 1H), 5.82 (d, J=2.6 Hz, 1H), 4.16-4.28 (m, 2H), 1.90 (t, J=7.3 Hz, 2H), 1.66 (t, J=7.7 Hz, 2H), 1.38-1.52 (m, 2H), 1.17-1.36 (m, 4H).

LCMS (ES): Found 357.4 $[M+H]^+$.

Example K

N-Hydroxy-7-[(pyrazin-2-yl)(pyrimidin-4-yl)amino]heptanamide

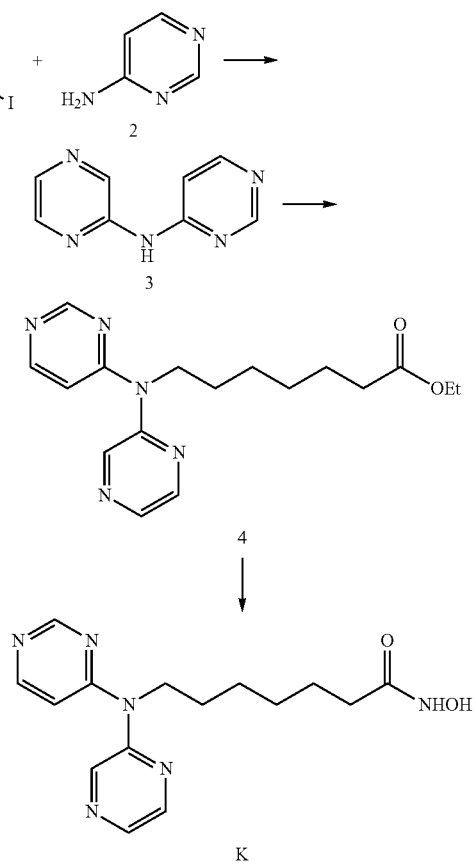

A solution of 2-iodopyrazine (1.2 g, 5.8 mmol), pyrimidin-4-amine (609 mg, 6.4 mmol), $Cs_2CO_3$ (3.8 g, 11.7 mmol) and Xantphos (148 mg, 0.26 mmol) in dioxane (15 mL) was purged with $N_2(g)$ for 10 min. $Pd_2(dba)_3$ (107 mg, 0.12 mmol) was added and the reaction mixture was sealed and heated up to 90° C. for 3 h. It was cooled to rt and partitioned between water (300 mL) and EtOAc (100 mL). Aqueous phases were separated and washed with EtOAc (2×100 mL). Combined organics were washed with water (50 mL), dried over $Na_2SO_4$, filtered and concentrated in vacuo. The residue was purified by flash column chromatography with $CH_2Cl_2$/MeOH (1:0-9:1) to yield (3) (678 mg, 66%).

$^1$H NMR (500 MHz, Methanol-$d_4$) $\delta_H$ ppm 9.06 (d, J=1.3 Hz, 1H), 8.74 (s, 1H), 8.42 (d, J=6.0 Hz, 1H), 8.34 (dd, J=2.6, 1.5 Hz, 1H), 8.19 (d, J=2.7 Hz, 1H), 7.72 (dd, J=6.0, 1.0 Hz, 1H).

LCMS (ES): Found 174.1 [M+H]$^+$.

$N_2(g)$. The reaction mixture was evaporated to dryness. The residue (off-white solid) was dissolved in MeOH and purified by reverse phase HPLC with $H_2O$:MeCN (1:0-0:1) to yield N-hydroxy-7-[(pyrazin-2-yl)(pyrimidin-4-yl)amino] heptanamide (K) as an off-white gum (79 mg, 35%).

$^1$H NMR (500 MHz, DMSO-$d_5$) $\delta_H$ ppm 8.83 (d, J=1.3 Hz, 1H), 8.69 (s, 1H), 8.51 (dd, J=2.4, 1.5 Hz, 1H), 8.33-8.43 (m, 2H), 7.00-7.05 (m, 1H), 4.01-4.14 (m, 2H), 1.89 (t, J=7.4 Hz, 2H), 1.60 (quin, J=7.5 Hz, 2H), 1.44 (quin, J=7.4 Hz, 2H), 1.17-1.33 (m, 4H).

LCMS (ES): Found 317.1 [M+H]$^+$.

Example L

2-{[6-(hydroxycarbamoyl)hexyl](3-methyl-1,2,4-thiadiazol-5-yl)amino}-N,N,6-trimethylpyrimidine-4-carboxamide

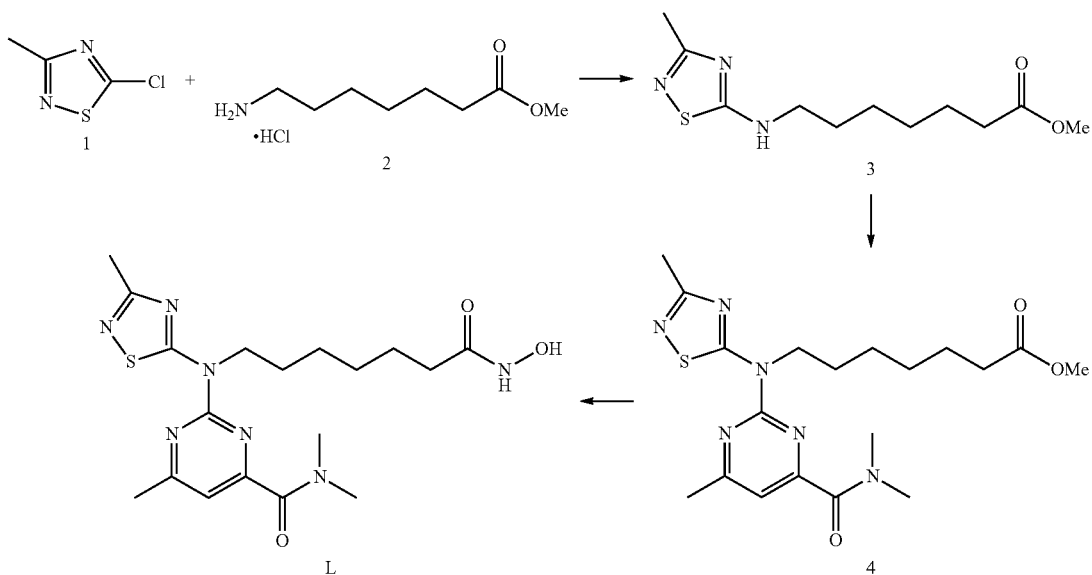

A suspension of N-(pyrimidin-4-yl)pyrazin-2-amine (3) (309 mg, 1.78 mmol) in dry DMF (7 mL) was cooled to 0° C. under $N_2(g)$. NaH (60% suspension, 75 mg, 1.87 mmol, 1.05 eq) was added in one portion and the mixture was stirred at 0° C. for 10 min. Then, the temperature was raised to ambient temperature and a solution of methyl 7-iodoheptanoate (578 mg, 2.14 mmol, 1.2 eq) in DMF (3 mL) was slowly added. The resulting mixture was heated to 70° C. and was stirred at that temperature for 1.5 h. After cooling to ambient temperature, the reaction mixture was quenched by adding onto $H_2O$ (50 mL). After extraction with EtOAc (3×30 mL), the combined organics were dried over $MgSO_4$, filtered and concentrated in vacuo. The residue was purified by flash column chromatography heptane/EtOAc (0:1-1:0) to yield (4) as light brown oil (230 mg, 41%).

$^1$H NMR (500 MHz, Chloroform-d) $\delta_H$ ppm 8.74-8.80 (m, 2H), 8.41 (dd, J=2.5, 1.5 Hz, 1H), 8.36 (d, J=6.0 Hz, 1H), 8.31 (d, J=2.6 Hz, 1H), 6.87 (dd, J=6.1, 1.2 Hz, 1H), 4.06-4.18 (m, 2H), 3.66 (s, 3H), 2.29 (t, J=7.5 Hz, 2H), 1.69-1.73 (m, 2H), 1.56-1.66 (m, 2H), 1.30-1.42 (m, 4H).

LCMS (ES): Found 316.1 [M+H]$^+$.

A solution of (4) (226 mg, 0.72 mmol) in 0.85M hydroxylamine in MeOH (10 mL) was stirred at rt for 18 h under A solution of (3) (100 mg, 0.37 mmol), 2-chloro-N,N,6-trimethylpyrimidine-4-carboxamide (110 mg, 0.55 mmol), $Cs_2CO_3$ (540 mg, 1.66 mmol), BINAP (14 mg, 0.02 mmol) in dry dioxane (2.5 mL) was degassed with $N_2(g)$ for 10 min. $Pd_2(dba)_3$ (10 mg, 0.01 mmol) was added and the mixture was heated up to 100° C. overnight. Once cooled, it was filtered through celite, washed with dioxane (2×5 mL) and the filtrate was concentrated in vacuo. The resulting residue was purified by basic prep-HPLC to yield (4) as a tan oil (117 mg, 78%).

To a solution of (4) (125 mg, 0.29 mmol) in MeOH/THF (1:1, 2 mL) was added hydroxylamine (50% w/w in $H_2O$; 0.35 mL, 5.8 mmol) followed by 6N NaOH (0.15 mL, 0.58 mmol). The mixture was stirred at rt for 20 min. The reaction was quenched with the addition of 1M $KHSO_4$ (2.0 mL) and $H_2O$ (5 mL). The aqueous layer was extracted with $CH_2Cl_2$ (2×5 mL). The organics were separated through a PTFE fritted tube then concentrated in vacuo. The resulting oil was purified by prep-HPLC to yield 2-{[6-(hydroxycarbamoyl) hexyl](3-methyl-1,2,4-thiadiazol-5-yl)amino}-N,N,6-trimethylpyrimidine-4-carboxamide (L) as a pale yellow oil (89 mg, 73%).

LCMS (ES): Found 422.5 [M+H]$^+$.

Example M

N-hydroxy-7-{[6-(methoxymethyl)pyrimidin-4-yl](3-methyl-1,2,4-thiadiazol-5-yl)amino}heptanamide

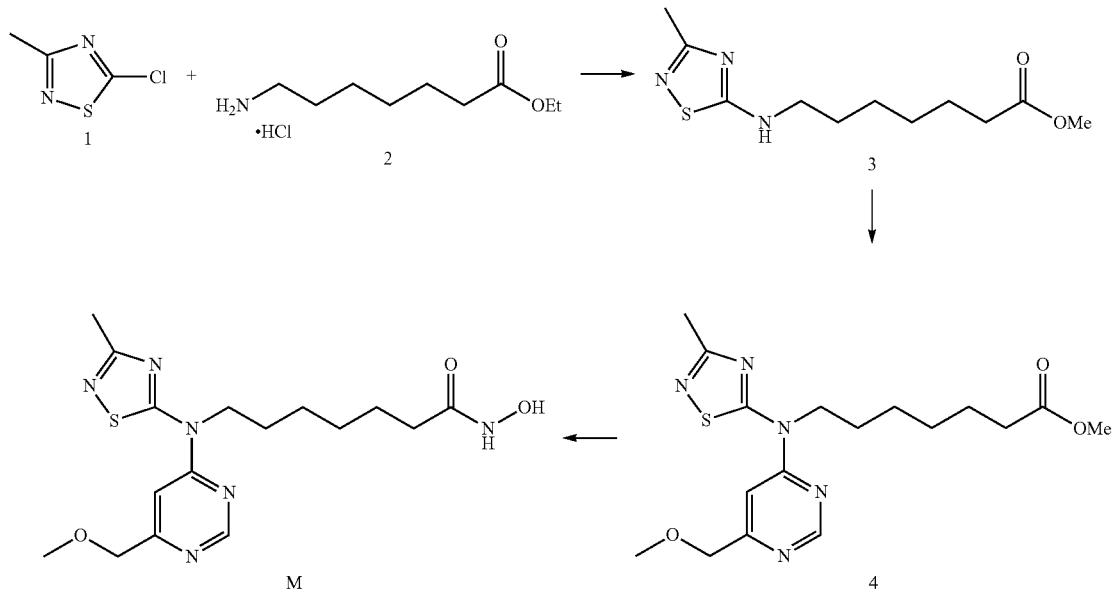

A solution of (3) (100 mg, 0.39 mmol), 4-chloro-6-(methoxymethyl)pyrimidine (74 mg, 0.47 mmol), $Cs_2CO_3$ (380 mg, 1.16 mmol), Xantphos (11 mg, 0.02 mmol) in dry dioxane (2.5 mL) was degassed with $N_2$(g) for 10 min. $Pd_2(dba)_3$ (11 mg, 0.01 mmol) was added and the mixture was heated up to 100° C. overnight. Once cooled down, it was filtered through celite, washed with dioxane (6×3 mL) and the filtrate was concentrated in vacuo. Purification by flash column chromatography with heptane/EtOAc (1:0-0:1) yielded (4) as an off-white solid (121 mg, 73%).

To a solution of (4) (121 mg, 0.32 mmol) in MeOH/THF (1:1, 2 mL) was added hydroxylamine (50% w/w in $H_2O$; 0.20 mL, 6.4 mmol) followed by 6N NaOH (0.1 mL, 0.6 mmol). The mixture was stirred at rt for 15 min. The reaction was quenched with the addition of 1M $KHSO_4$ (2.0 mL) and $H_2O$ (5 mL). The resulting suspension was stirred for 10 min before the solid was collected by filtration, washing the cake with $H_2O$ (2×5 mL). The residue was purified by prep-HPLC to yield N-hydroxy-7-{[6-(methoxymethyl)pyrimidin-4-yl](3-methyl-1,2,4-thiadiazol-5-yl)amino}heptanamide (M) as an orange solid (46 mg, 38%).

LCMS (ES): Found 381.5 $[M+H]^+$.

Example N

N-hydroxy-7-({5-methyl-5H-pyrrolo[3,2-d]pyrimidin-4-yl}(pyrazin-2-yl)amino) heptanamide

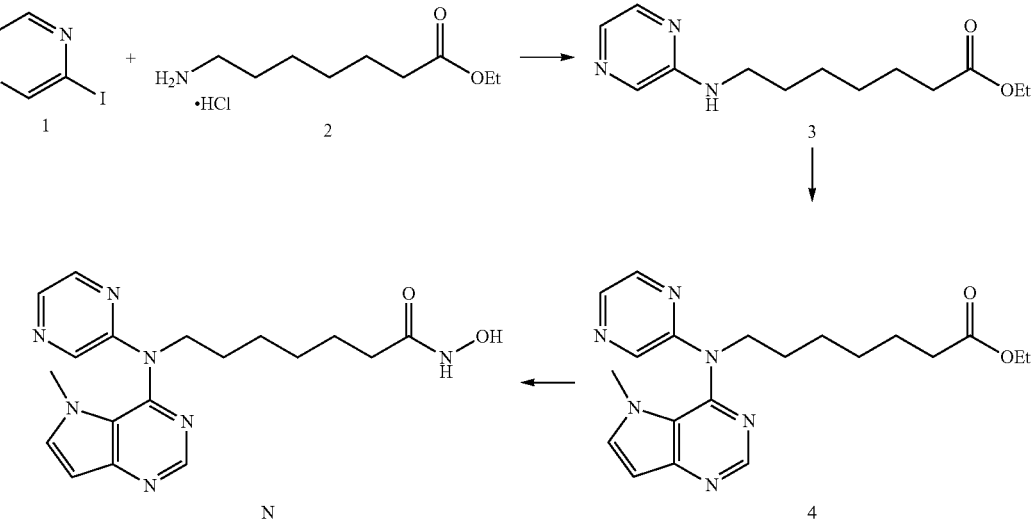

A solution of (3) (100 mg, 0.40 mmol), 4-chloro-5-methyl-5H-pyrrolo[3,2-d]pyrimidine (100 mg, 0.60 mmol), Cs$_2$CO$_3$ (389 mg, 1.2 mmol) and BINAP (15 mg, 0.02 mmol) in dioxane (4 mL) was purged with Ar(g) for 10 min. Pd$_2$(dba)$_3$ (11 mg, 0.012 mmol) was added and the mixture was heated up to 100° C. overnight. The reaction was then re-charged with 4-chloro-5-methyl-5H-pyrrolo[3,2-d]pyrimidine (100 mg, 0.60 mmol), Pd(OAc)$_2$ (12 mg, 0.05 mmol) and Xantphos (13 mg, 0.03 mmol). It was heated up to 100° C. another night. Once cooled down, it was filtered through celite, washed with dioxane (6×3 mL) and the filtrate was concentrated in vacuo. Purification by flash column chromatography with heptane/EtOAc (1:0-0:1) then EtOAc/MeOH (1:0-4:1) yielded (4) as a brown residue (159 mg, 50%).

To a solution of (4) (159 mg, 0.42 mmol) in MeOH/THF (1:1, 2 mL) was added hydroxylamine (50% w/w in H$_2$O; 0.50 mL, 8.3 mmol) followed by 6N NaOH (0.14 mL, 0.8 mmol). The mixture was stirred at rt for 15 min. The reaction was quenched with the addition of 1M KHSO$_4$ (2.0 mL) and H$_2$O (5 mL). The aqueous layer was extracted with CH$_2$Cl$_2$ (2×5 mL). The organics were separated through a PTFE fritted tube then concentrated in vacuo. The residue was purified by neutral prep-HPLC to yield N-hydroxy-7-({5-methyl-4aH,5H,7aH-pyrrolo[3,2-d]pyramidin-4-yl}(pyrazin-2-yl)amino)heptanamide (N) as a pale yellow foam (2.7 mg, 1.7%).

LCMS (ES): Found 370.2 [M+H]$^+$.

Example O

7-{[6-(dimethylamino)pyridazin-3-yl](pyrazin-2-yl)amino}-N-hydroxyheptanamide

A solution of (3) (100 mg, 0.40 mmol), 6-bromo-N,N-dimethylpyridazin-3-amine (96.4 mg, 0.48 mmol), Cs$_2$CO$_3$ (389 mg, 1.2 mmol) and BINAP (15 mg, 0.02 mmol) in dioxane (4 mL) was purged with Ar(g) for 10 min. Pd$_2$(dba)$_3$ (11 mg, 0.012 mmol) was added and the mixture was heated up to 100° C. overnight. The mixture was then re-charged with Cs$_2$CO$_3$ (300 mg, 0.92 mmol), Xantphos (4.3 mg, 0.01 mmol) and Pd(OAc)$_2$ (4.7 mg, 0.02 mmol). Once cooled down, the mixture was diluted with CH$_2$Cl$_2$ (3 mL), filtered through celite, washed with CH$_2$Cl$_2$ (6×3 mL) and the filtrate was concentrated in vacuo. Purification by flash column chromatography with heptane/EtOAc (1:0-0:1) then CH$_2$Cl$_2$/MeOH (1:0-9:1) yielded (4) as a black gum (108 mg, 42%).

To a solution of (4) (108 mg, 0.29 mmol) in MeOH/THF (1:1, 2 mL) was added hydroxylamine (50% w/w in H$_2$O; 0.18 mL, 6.0 mmol) followed by 6N NaOH (0.1 mL, 0.58 mmol). The mixture was stirred at rt for 15 min. The reaction was quenched with the addition of 1M KHSO$_4$ (2.0 mL) and H$_2$O (5 mL). The aqueous layer was extracted with IPA:chloroform (1:2, 2×30 mL). The organics were then concentrated in vacuo. The residue was purified by prep-HPLC to yield 7-{[6-(dimethylamino)pyridazin-3-yl](pyrazin-2-yl)amino}-N-hydroxyheptanamide (O) as a yellow glass film (41.1 mg, 34%).

$^1$H NMR (500 MHz, DMSO-d$_5$) δ$_H$ ppm 10.30 (br. s., 1H), 8.62 (br. s., 1H), 8.13-8.15 (m, 1H), 8.06-8.08 (m, 1H), 7.93 (d, J=2.7 Hz, 1H), 7.39-7.45 (m, 1H), 7.17 (d, J=9.6 Hz, 1H), 3.96-4.00 (m, 2H), 3.10-3.12 (m, 6H), 1.91 (t, J=7.4 Hz, 2H), 1.54-1.62 (m, 2H), 1.40-1.48 (m, 2H), 1.19-1.31 (m, 4H).

LCMS (ES): Found 360.2 [M+H]$^+$.

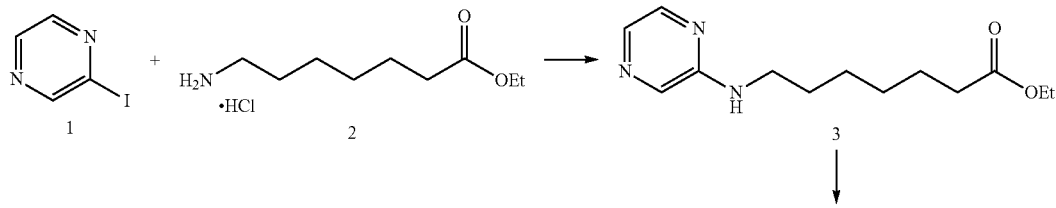

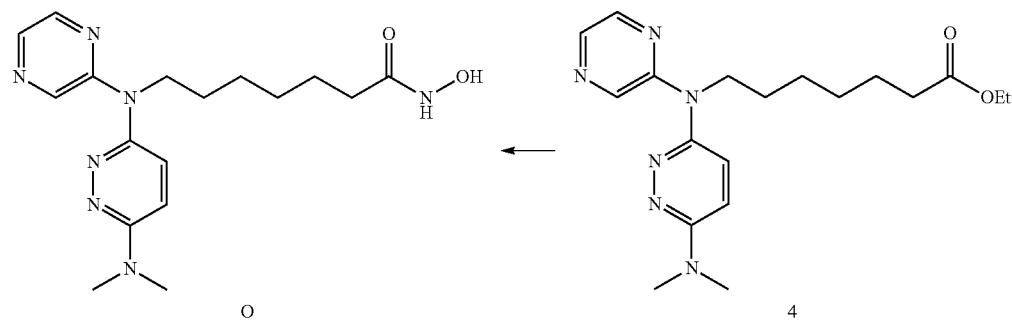

Example P

N-hydroxy-7-({1-methyl-1H-pyrazolo[4,3-d]pyrimidin-7-yl}(pyrazin-2-yl)amino)heptanamide

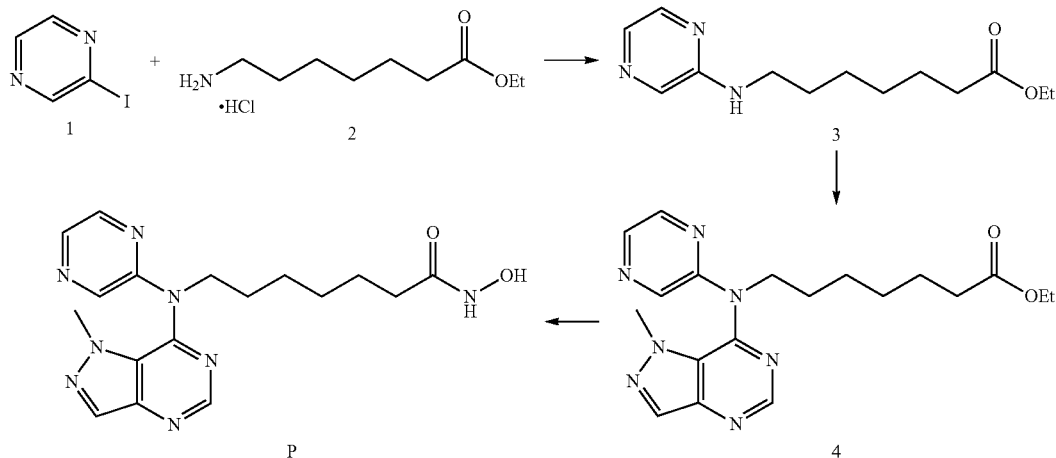

A solution of (3) (100 mg, 0.40 mmol), 7-chloro-1-methyl-1H-pyrazolo[4,3-d]pyrimidine (80.5 mg, 0.48 mmol), Cs$_2$CO$_3$ (389 mg, 1.2 mmol) and BINAP (15 mg, 0.02 mmol) in dioxane (3 mL) was purged with Ar(g) for 10 min. Pd$_2$(dba)$_3$ (11 mg, 0.012 mmol) was added and the mixture was heated up to 100° C. overnight. The reaction was then re-charged with 7-chloro-1-methyl-1H-pyrazolo[4,3-d]pyrimidine (40.0 mg, 0.24 mmol), Pd(OAc)$_2$ (4.5 mg, 0.02 mmol) and Xantphos (4.3 mg, 0.01 mmol). It was heated up to 100° C. for another night. The reaction was again re-charged with Cs$_2$CO$_3$ (300 mg, 0.9 mmol), Pd(OAc)$_2$ (4.5 mg, 0.02 mmol) and Xantphos (4.3 mg, 0.01 mmol), then heated up to 100° C. for another night. Once cooled down, the mixture was diluted with CH$_2$Cl$_2$ (3 mL), filtered through celite, washed with CH$_2$Cl$_2$ (6×3 mL) and the filtrate was concentrated in vacuo. Purification by flash column chromatography with heptane/EtOAc (1:0-0:1) then CH$_2$Cl$_2$/MeOH (1:0-9:1) yielded (4) as an orange oil (72 mg, 28%).

LCMS (ES): Found 384.5 [M+H]$^+$.

To a solution of (4) (72 mg, 0.19 mmol) in MeOH/THF (1:1, 2 mL) was added hydroxylamine (50% w/w in H$_2$O; 0.12 mL, 3.8 mmol) followed by 6N NaOH (0.06 mL, 0.38 mmol). The mixture was stirred at rt for 15 min. The reaction was quenched with the addition of 1M KHSO$_4$ (2 mL) and H$_2$O (7 mL). The aqueous layer was extracted with CH$_2$Cl$_2$ (2×10 mL). The organics were separated through a PTFE fritted tube then concentrated in vacuo. The residue was purified by prep-HPLC to yield N-hydroxy-7-({1-methyl-1H-pyrazolo[4,3-d]pyrimidin-7-yl}(pyrazin-2-yl)amino)heptanamide (P) as an off-white solid (2.5 mg, 4%).

LCMS (ES): Found 371.1 [M+H]$^+$.

Example Q

7-{[5-(dimethylamino)pyrazin-2-yl](pyrazin-2-yl)amino}-N-hydroxyheptanamide

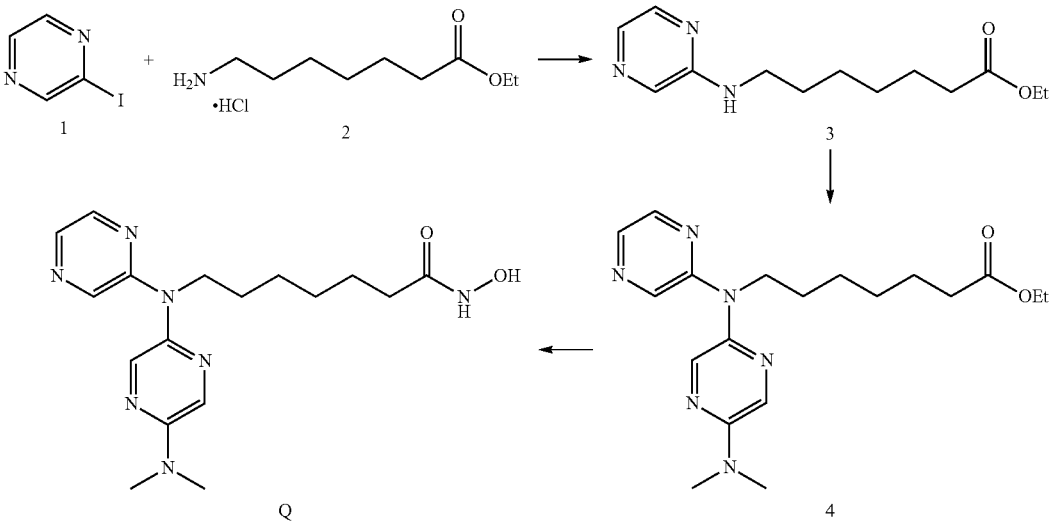

A solution of (3) (100 mg, 0.40 mmol), 5-bromo-N,N-dimethylpyrazin-2-amine (96.5 mg, 0.48 mmol), Cs$_2$CO$_3$ (389 mg, 1.2 mmol) and BINAP (15 mg, 0.02 mmol) in dioxane (3 mL) was purged with Ar(g) for 10 min. Pd$_2$(dba)$_3$ (11 mg, 0.012 mmol) was added and the mixture was heated up to 100° C. overnight. The reaction was then re-charged with 5-bromo-N,N-dimethylpyrazin-2-amine (45 mg, 0.22 mmol), Pd(OAc)$_2$ (4.5 mg, 0.02 mmol) and Xantphos (4.3 mg, 0.01 mmol). It was heated up to 100° C. for another night. The reaction was again re-charged with Cs$_2$CO$_3$ (300 mg, 0.9 mmol), Pd(OAc)$_2$ (4.5 mg, 0.02 mmol) and Xantphos (4.3 mg, 0.01 mmol), then heated up to 100° C. for another night. Once cooled down, the mixture was diluted with CH$_2$Cl$_2$ (3 mL), filtered through celite, washed with CH$_2$Cl$_2$ (6×3 mL) and the filtrate was concentrated in vacuo. Purification by flash column chromatography with CH$_2$Cl$_2$/MeOH (1:0-9:1) yielded (4) as a brown gum (171 mg, 49%).

LCMS (ES): Found 373.1 [M+H]$^+$.

To a solution of (4) (171 mg, 0.46 mmol) in MeOH/THF (1:1, 2 mL) was added hydroxylamine (50% w/w in H$_2$O; 0.28 mL, 9.2 mmol) followed by 6N NaOH (0.15 mL, 0.92 mmol). The mixture was stirred at rt for 15 min. The reaction was quenched with the addition of 1M KHSO$_4$ (2 mL) and H$_2$O (7 mL). The aqueous layer was extracted with CH$_2$Cl$_2$ (2×10 mL). The organics were separated through a PTFE fritted tube then concentrated in vacuo. The residue was purified by neutral prep-HPLC to yield 7-{[5-(dimethylamino)pyrazin-2-yl](pyrazin-2-yl)amino}-N-hydroxyheptanamide (Q) as an off-white solid (38 mg, 23%).

LCMS (ES): Found 360.2 [M+H]$^+$.

Example R

N-hydroxy-7-[(pyrazin-2-yl)(pyrimidin-5-yl)amino]heptanamide

A solution of (3) (100 mg, 0.40 mmol), 5-bromopyrimidine (94.9 mg, 0.60 mmol), Cs$_2$CO$_3$ (389 mg, 1.2 mmol), BINAP (15 mg, 0.02 mmol) and Pd$_2$(dba)$_3$ (11 mg, 0.012 mmol) in dioxane (2.5 mL) was purged with Ar(g) for 10 min. Then, Pd(OAc)$_2$ (12 mg, 0.05 mmol) and Xantphos (13 mg, 0.03 mmol) were added and the mixture was heated up to 100° C. overnight. The reaction was then re-charged with Pd(OAc)$_2$ (12 mg, 0.05 mmol) and Xantphos (13 mg, 0.03 mmol). It was heated up to 100° C. for another night. Once cooled down, the mixture was diluted with dioxane (3 mL), filtered through celite, washed with dioxane (3×3 mL) and the filtrate was concentrated in vacuo. Purification by basic prep-HPLC yielded (4) as a tan residue (82 mg, 50% pure, 31%), which was used as such in the next step.

To a solution of (4) (82 mg, 50% pure, 0.12 mmol) in MeOH/THF (1:1, 1 mL) was added hydroxylamine (50% w/w in H$_2$O; 0.15 mL, 2.4 mmol) followed by 6N NaOH (0.04 mL, 0.24 mmol). The mixture was stirred at rt for 15 min. The reaction was quenched with the addition of 1M KHSO$_4$ (2 mL) and H$_2$O (5 mL). The aqueous layer was extracted with CH$_2$Cl$_2$ (2×5 mL). The organics were separated through a PTFE fritted tube then concentrated in vacuo. The residue was purified by prep-HPLC to yield N-hydroxy-7-[(pyrazin-2-yl)(pyrimidin-5-yl)amino]heptanamide (R) as a pale yellow oil (9.8 mg, 25%).

LCMS (ES): Found 317.1 [M+H]$^+$.

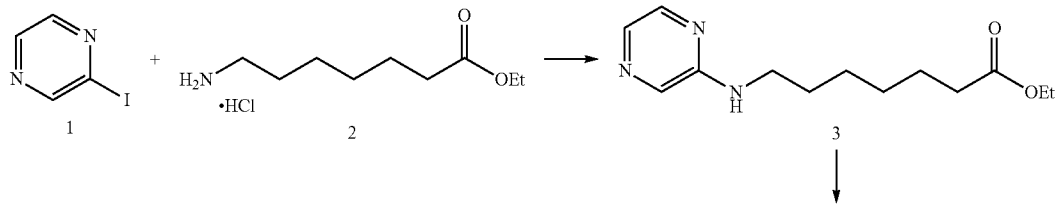

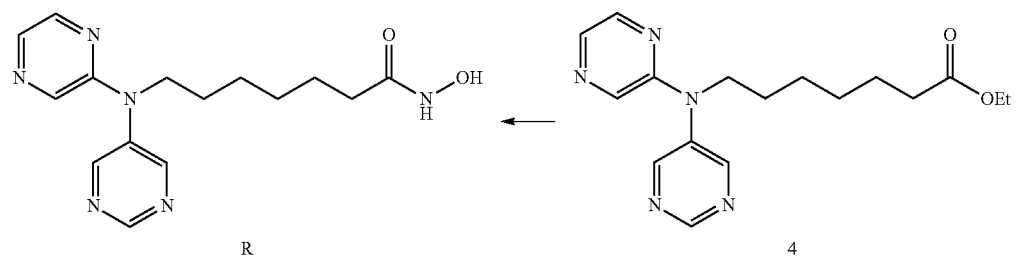

Example S

N-hydroxy-7-[(3-methyl-1,2,4-oxadiazol-5-yl)[6-(morpholin-4-yl)pyrazin-2-yl]amino]heptanamide

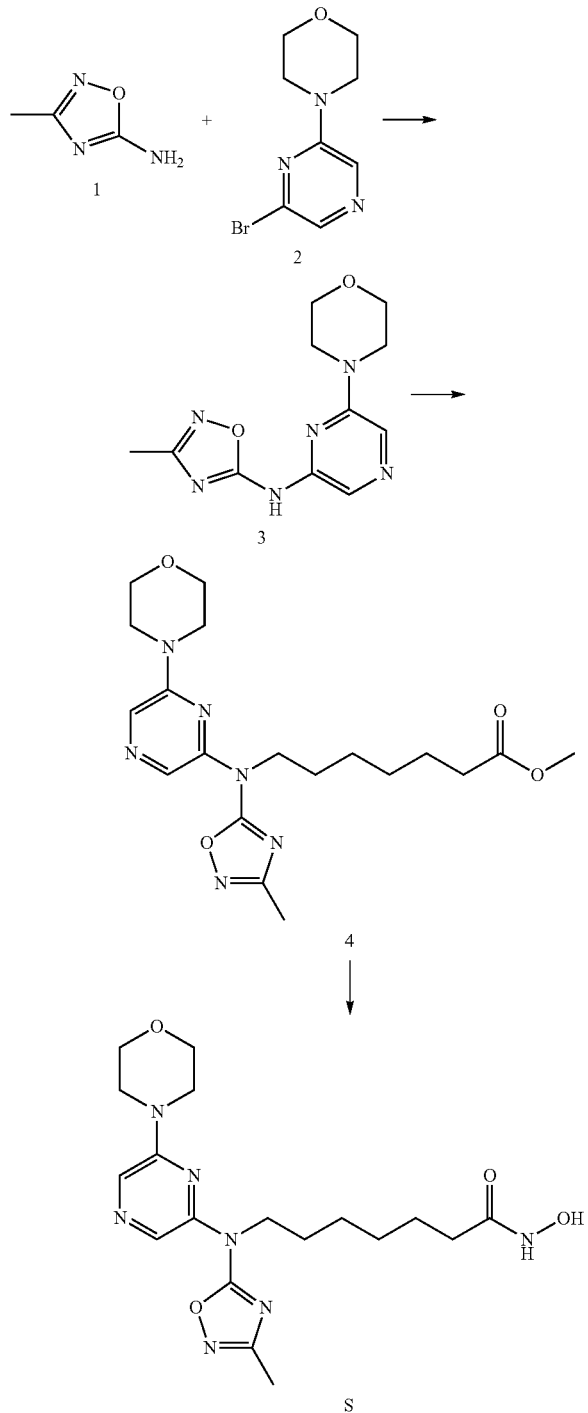

A solution of 3-methyl-1,2,4-oxadiazol-5-amine (120 mg, 1.2 mmol), 4-(6-bromopyrazin-2-yl)morpholine (355 mg, 1.45 mmol), $Cs_2CO_3$ (986 mg, 3.0 mmol) and Xantphos (28 mg, 0.05 mmol) in dioxane (3 mL) was purged with $N_2(g)$ for 10 min. $Pd_2(dba)_3$ (22 mg, 0.02 mmol) was added and the reaction mixture was heated up to 100° C. overnight. Once cooled down, it was diluted with dioxane (5 mL) and filtered. The precipitate was taken up in $H_2O$ (5 mL), sonicated, filtered and washed with $H_2O$ (3×10 mL). Additional material was recovered from the aqueous layer after purification by basic prep-HPLC. Both materials were combined to yield (3) as a grey powder (139 mg, 42%).

LCMS (ES): Found 263.4 $[M+H]^+$.

To NaH (60% suspension, 32 mg, 0.8 mmol) in dry DMF (7 mL) was added dropwise a solution of (3) (139 mg, 0.53 mmol) in DMF (2 mL) at 0° C. under $N_2(g)$. The mixture was then warmed to rt for 10 min and a solution of methyl 7-iodoheptanoate (186 mg, 0.69 mmol) in DMF (1 mL) was slowly added. The resulting mixture was heated up to 70° C. for 1 h in dark. Once cooled down, the reaction mixture was quenched with $H_2O$ (30 mL) and extracted with EtOAc (4×10 mL). The combined organics were washed with brine, dried over $Na_2SO_4$, filtered and concentrated in vacuo. The residue was purified by flash column chromatography heptane/EtOAc (4:1-2:3) to yield (4) as a yellow oil (153 mg, 68%).

$^1$H NMR (500 MHz, Chloroform-d) $\delta_H$ ppm 8.65 (br. s., 1H), 7.87 (br. s., 1H), 4.09-4.20 (m, 2H), 3.80-3.87 (m, 4H), 3.66 (s, 3H), 3.49-3.58 (m, 4H), 2.31 (s, 3H), 2.28 (t, J=7.5 Hz, 2H), 1.74 (t, J=7.4 Hz, 2H), 1.53-1.67 (m, 2H), 1.28-1.42 (m, 4H).

LCMS (ES): Found 263.1 $[M+H]^+$.

To a solution of (4) (140 mg, 0.35 mmol) in MeOH/THF (1:1, 3 mL) was added hydroxylamine (50% w/w in $H_2O$; 0.42 mL, 7.0 mmol) followed by 6N NaOH (0.12 mL, 0.70 mmol). The mixture was stirred at rt for 15 min. The reaction was quenched with the addition of 1M $KHSO_4$ (5 mL) and $H_2O$ (10 mL). The aqueous layer was extracted with $CH_2Cl_2$ (4×10 mL). The organics were dried over $Na_2SO_4$, filtered and concentrated in vacuo to yield N-hydroxy-7-[(3-methyl-1,2,4-oxadiazol-5-yl)[6-(morpholin-411)pyrazin-2-yl]amino]heptanamide (S) as a pale yellow wax (101 mg, 71%).

$^1$H NMR (500 MHz, DMSO-$d_5$) $\delta_H$ ppm 10.32 (br. s., 1H), 8.65 (br. s., 1H), 8.47 (s, 1H), 8.07 (s, 1H), 3.99-4.13 (m, 2H), 3.68-3.77 (m, 4H), 3.48-3.56 (m, 4H), 2.24 (s, 3H), 1.92 (t, J=7.3 Hz, 2H), 1.64 (quin, J=7.2 Hz, 2H), 1.45 (quin, J=7.3 Hz, 2H), 1.18-1.34 (m, 4H).

LCMS (ES): Found 406.5 $[M+H]^+$.

| Biochemical Selectivity | | |
|---|---|---|
| Example | HDAC1 | HDAC6 |
| A | *** | * |
| B | *** | * |
| C | ** | * |
| D | ** | * |
| E | ** | * |
| F | ** | * |
| G | ** | * |
| H | *** | * |
| I | *** | * |
| J | *** | * |
| K | ** | ** |
| L | ** | * |
| M | *** | * |
| N | *** | * |
| O | ** | * |
| P | *** | * |
| Q | ** | * |
| R | *** | * |
| S | *** | * |

Key:
*≤100 nM
**>100 nM ≤ 1000 nM
***>1000 nM

Comparative Plasma Clearance Data Following IV Treatment for Example

When comparing compounds of the present invention with Examples in WO 2010/086646 and WO 2014/072714, it has been shown that compounds of the invention have improved plasma clearance following IV dosing in mice.

Example D

Protocol

A group of eighteen male Balb/c mice were divided into two groups Group 1 (3 mg/kg; i.v.), Group 2 (10 mg/kg; p.o.) with each group comprising of nine mice. Animals in Group 1 were administered intravenously with Example D solution formulation in 5% NMP, 5% solutol HS-15 in 90% HPβCD solution (20% HPβCD in RO water) at 3 mg/kg dose while animals in Group 2 were administered orally with 10 mg/kg solution formulation of Example D in 5% NMP, 5% solutol HS-15 in 90% HPβCD solution (20% HPβCD in RO water). Blood samples (approximately 60 μL) were collected from retro orbital plexus under light isoflurane anesthesia such that the samples were obtained at pre-dose, 0.08, 0.25, 0.5, 1, 2, 4, 8 and 24 hr (i.v.) and pre-dose, 0.25, 0.5, 1, 2, 4, 6, 8 and 24 hr (p.o.). The blood samples were collected from set of three mice at each time point in labeled micro centrifuge tube containing $K_2$EDTA as anticoagulant. Plasma samples were separated by centrifugation of whole blood and stored below −70° C. until bioanalysis. All samples were processed for analysis by protein precipitation using acetonitrile (ACN) and analyzed with fit for purpose LC/MS/MS method (LLOQ: 1.27 ng/mL). Pharmacokinetic parameters were calculated using the non-compartmental analysis tool of Phoenix WinNonlin (Version 6.3).

Plasma clearance=48.60 mL/min/kg

Example 3 of WO 2010/086646

Protocol

Compound was administered both intravenously and orally to mice. Blood samples were collected at up to 7 time points over 8 hours and plasma was analysed by LC-MS/MS to determine the concentration of compound at each time point. The plasma time concentration profile was delivered along with the main calculated PK parameters (Co, Cmax, AUC-last, $t_{1/2}$, tmax, Vd, and CL).

Three male CD1 mice, 25-30 g, were dosed per administration route per timepoint. Compound was administered both orally (10 mg compound per kg of body weight) and intravenously (5 mg compound per kg body weight). The excipient used was 10% NMP/90% water. Animals were given free access to food throughout the study.

At the following time points, the animals were anaesthetized, blood collected in heparinized tubes and animals were sacrificed:

Oral dosing: 0.08, 0.25, 0.5, 1, 2, 4 and 8 hr post-dose;
IV dosing: 0.08, 0.25, 0.5, 1, 2, 4 and 8 hr post-dose.

Blood samples were centrifuged to obtain the plasma, which was transferred to a separate, labelled container. Aliquots from the individual time points for the three animals were analyzed singly. Protein was precipitated by adding three volumes of methanol and centrifuging for 30 min at 4° C. Aliquots of 100 μL of the resulting supernatant were diluted with 200 μL of HPLC grade water in a 96 well plate. Standard curves were prepared in blank plasma matrices and treated in an identical manner to the samples. The plasma samples were quantified by LC-MS/MS and the concentration of compound in plasma was reported in μg/mL. Pharmacokinetic parameters were calculated employing non-compartmental model analysis.

Plasma clearance=373.76 mL/min/kg

Example A of WO 2014/072714

Protocol
Species: Mouse
Strain: CD1
Sex: Male
Formulation: Solutions in 10% DMSO, 15% Cremophor, 75% Saline
Dosing: 10 mg/kg P.O. and 5 mg/kg I.V.
Protocol:
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of AUC, AUMC, Vss, CL, half life, MRT and bioavailability.

Plasma clearance=252.8 mL/min/kg

The invention claimed is:

1. A compound of the formula wherein:
- - - is a single bond and X is N; and wherein:
n is 3 to 7;
R is H;
each R′ is independently selected from H and QR$_1$;
each Q is independently selected from the group consisting of a bond, C$_1$-C$_4$ alkylene, CO, CO$_2$, NH, S, SO, SO$_2$ and O;
each R$_1$ is independently selected from the group consisting of H, C$_1$-C$_{10}$ alkyl, C$_2$-C$_{10}$ alkenyl, C$_2$-C$_{10}$ alkynyl, C$_1$-C$_4$ alkoxy, aryl, heteroaryl, C$_1$-C$_{10}$ cycloalkyl, halogen, C$_1$-C$_{10}$ alkylaryl, C$_1$-C$_{10}$ alkyl heteroaryl, C$_1$-C$_{10}$ heterocycloalkyl, NR$_2$R$_3$ and trifluoromethyl, wherein R$_2$ and R$_3$ are C$_1$-C$_4$ alkyl;
each L is independently a 5- to 12-membered heteroaryl, wherein each L contains at least two nitrogen atoms, wherein at least one L is pyrazinyl or pyrimidinyl;
W is

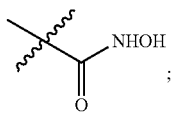

;

each aryl or heteroaryl may be substituted by up to five substituents independently selected from the group consisting of C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis(C$_1$-C$_3$ alkyl) amino C$_1$-C$_3$ alkyl, C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl and bis C$_1$-C$_3$-alkyl aminosulfonyl; and each alkyl, alkenyl or alkynyl may be optionally substituted with a substituent selected from the group consisting of C$_1$-C$_{10}$ alkyl, C$_2$-C$_{10}$ alkenyl, C$_2$-C$_{10}$ alkynyl, aryl, cycloalkyl, heteroaryl, halogen, NH$_2$, NO$_2$ and hydroxyl, or a pharmaceutically acceptable salt thereof.

2. The compound according to claim 1, wherein
R′ is independently selected from H and QR$_1$;
each Q is independently selected from the group consisting of a bond, CO, CO$_2$, NH, S, SO, SO$_2$ and O; and
each R$_1$ is independently selected from the group consisting of H, C$_1$-C$_{10}$ alkyl, C$_2$-C$_{10}$ alkenyl, C$_2$-C$_{10}$ alkynyl, aryl, heteroaryl, C$_1$-C$_{10}$ cycloalkyl, halogen, C$_1$-C$_{10}$ alkylaryl, C$_1$-C$_{10}$ alkyl heteroaryl, C$_1$-C$_{10}$ heterocycloalkyl, and trifluoromethyl.

3. The compound according to claim 1, wherein one L is independently selected from the group consisting of pyrazolyl, pyrazinyl, pyrimidinyl, pyridazinyl, thiadiazolyl, oxadiazolyl and imidazolyl, each of which may be optionally fused to a 5-membered heteroaryl, wherein the 5-membered heteroaryl contains at least one N or O.

4. The compound according to claim 1, wherein one L is independently selected from the group consisting of pyrazolyl, pyrazinyl, pyrimidinyl, pyridazinyl, thiadiazolyl and imidazolyl, each of which may be optionally fused to a 5-membered nitrogen-containing heteroaryl, wherein the 5-membered heteroaryl contains N.

5. The compound according to claim 1, wherein in at least one of L, the atom that is directly bonded to X is a carbon, and at least one nitrogen atom is directly bonded to said carbon.

6. The compound according to claim 1, wherein one L is a 6-membered heteroaryl independently selected from the group consisting of pyrazinyl, pyrimidinyl, and pyridazinyl.

7. The compound according to claim 1, wherein R′ is independently selected from the group consisting of H, C$_1$-C$_{10}$ alkyl, O—(C$_1$-C$_{10}$ alkyl), N(C$_1$-C$_4$ alkyl)$_2$, C$_1$-C$_{10}$heterocycloalkyl, trifluoromethyl and halogen, wherein the alkyl may be substituted with at least one fluorine.

8. The compound according to claim 7, wherein the C$_1$-C$_{10}$heterocycloalkyl is morpholino.

9. The compound according to claim 7, wherein R′ is independently H or CF$_3$.

10. The compound according to claim 1, wherein n is 5 to 7.

11. A compound represented by:

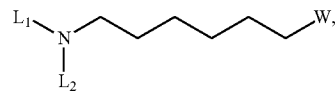

or a pharmaceutically acceptable salt thereof,
wherein
L$_1$ is a 5-6 membered monocyclic heteroaryl having at least 2 nitrogen atoms;
L$_2$ is a 5-6 membered monocyclic heteroaryl having at least 2 nitrogen atoms, or a 9-10 membered bicyclic heteroaryl having at least 2 nitrogen atoms; wherein L$_1$ and L$_2$ are each optionally substituted by one, two or three substituents each independently selected from RL;
RL is selected for each occurrence from the group consisting of: C$_{1-6}$alkyl, C$_{2-6}$alkenyl, C$_{2-6}$alkynyl; C$_{1-6}$alkoxy, C$_{3-6}$cycloalkyl, halogen, NR$^a$R$^b$; —C(O)—NR$^a$R$^b$, —NR$^a$C(O)—R$^a$; and —NR$^a$SO$_2$—R$^a$, wherein the C$_{1-6}$alkyl, C$_{2-6}$alkenyl, C$_{2-6}$alkynyl, C$_{1-6}$alkoxy and C$_{3-6}$cycloalkyl may be optionally substituted by one, two or three substituents selected independently from halogens and C$_{1-6}$alkoxy;
R$^a$ and R$^b$ are each independently selected from H and C$_{1-4}$alkyl; or R$^a$ and R$^b$ taken together with the nitrogen to which they are attached form a 4-6 membered heterocycle; and
W is a zinc binding group.

12. The compound of claim 11, represented by:

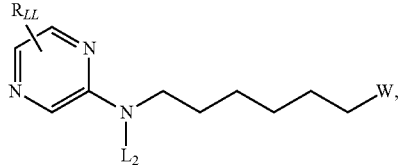

wherein R$_{LL}$ is selected for each occurrence from the group consisting of H, F, CF$_3$, and CH$_3$.

13. The compound of claim 11, wherein $L_2$ is a 6 membered monocyclic heteroaryl having two nitrogens.

14. The compound of claim 11, represented by:

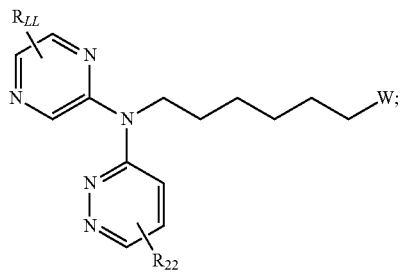

wherein $R_{LL}$ is selected from the group consisting of H, F, $CF_3$, and $CH_3$; $R_{22}$ is selected from the group consisting of H, F, $NR^aR^b$, $C_{1-2}$alkoxy, and methoxymethyl.

15. The compound of claim 11, wherein W is selected from the group consisting of: —C(O)NHOH, and —C(O)—O—$C_{1-2}$alkyl.

16. A compound selected from the group consisting of

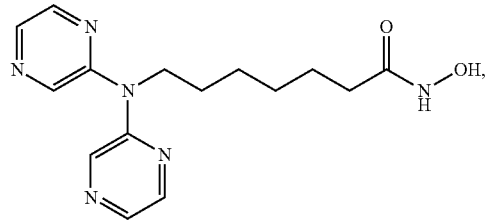

A

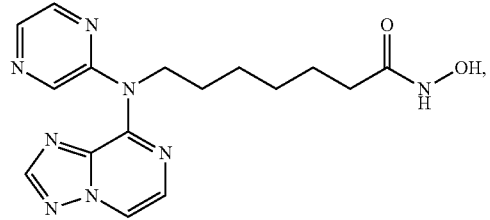

B

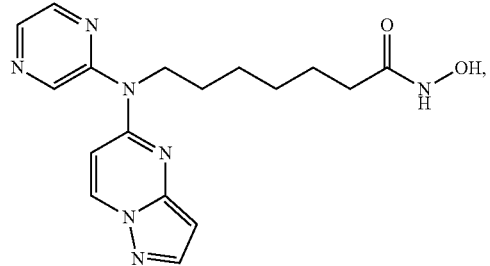

C

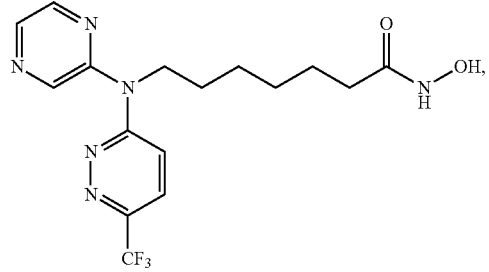

D

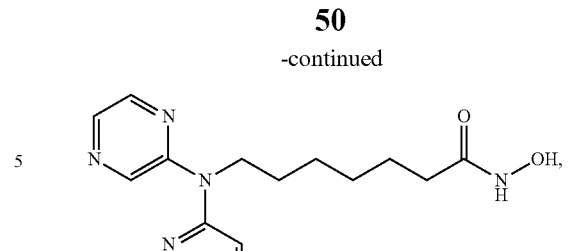

E

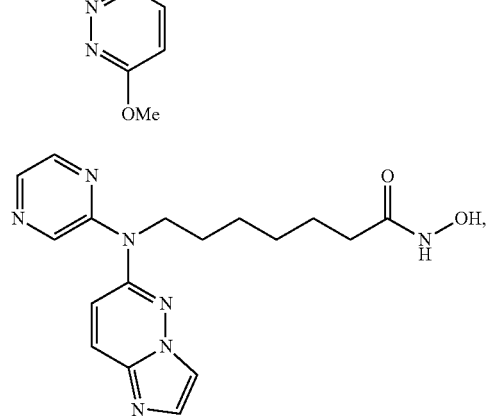

F

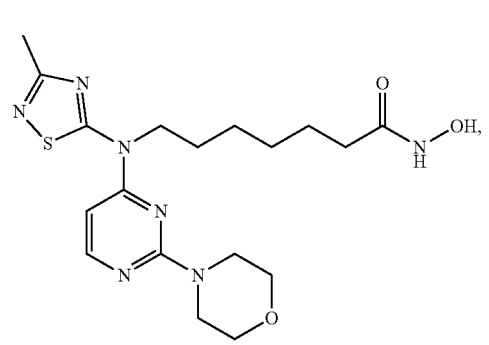

G

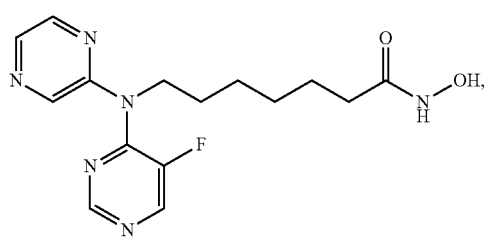

H

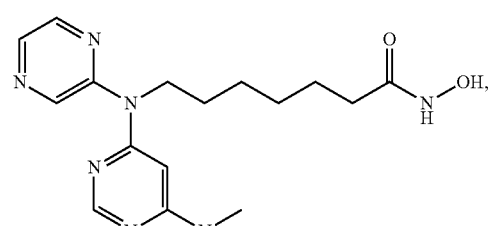

I

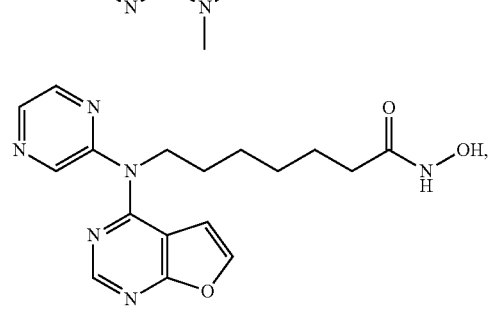

J

51

-continued

K
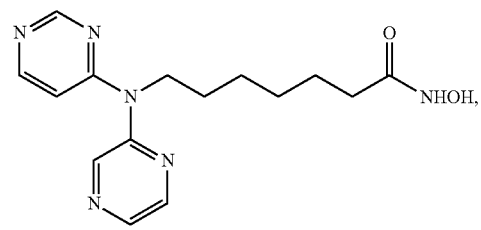

L
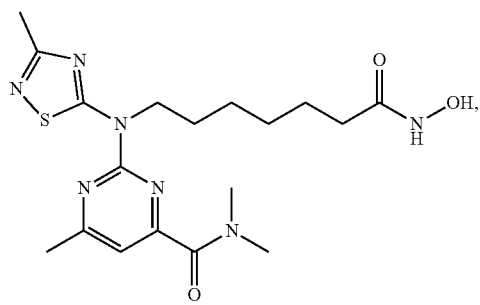

M
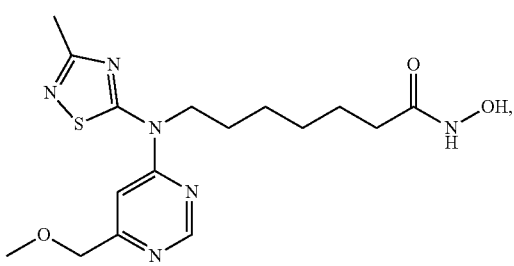

N
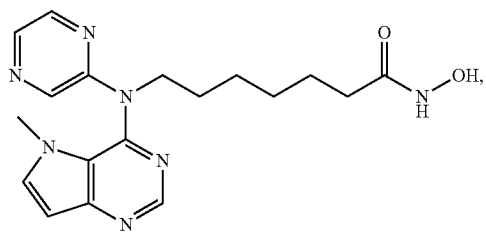

O
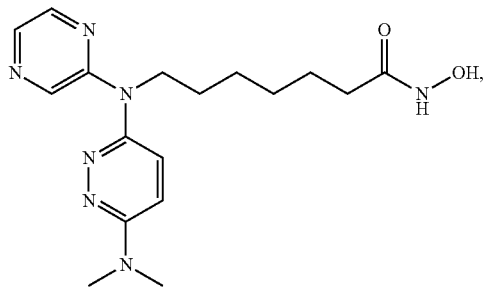

P
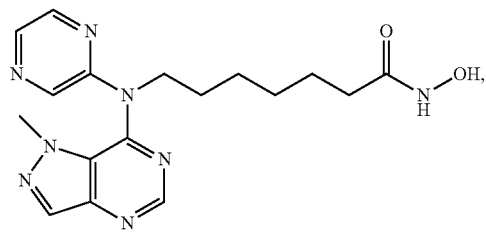

52

-continued

Q
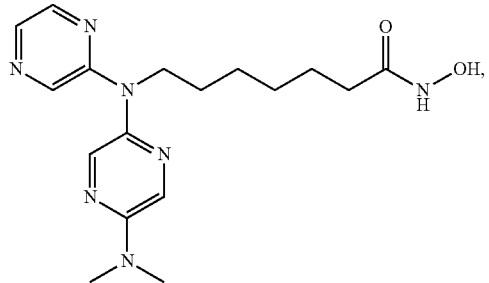

R
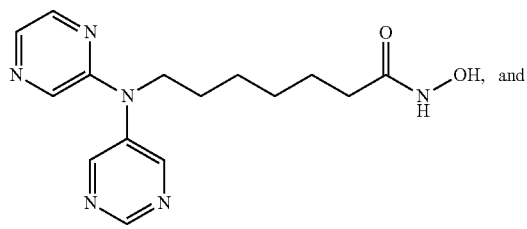

S
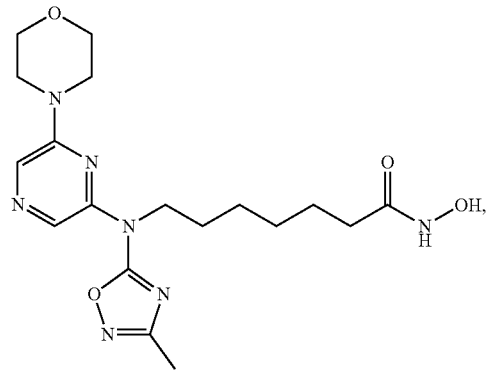

or a pharmaceutically acceptable salt thereof.

17. The compound of claim 16, wherein the compound is

D
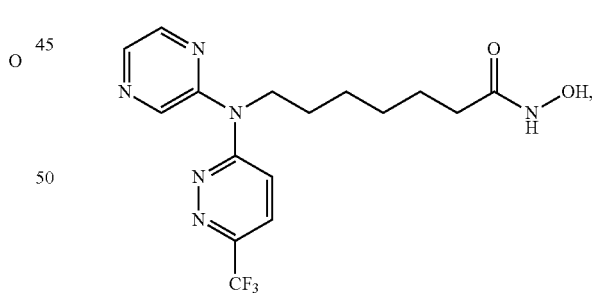

or a pharmaceutically acceptable salt thereof.

18. A pharmaceutical composition comprising a compound according to claim 1, and a pharmaceutically acceptable carrier or diluent.

19. A method of treating a condition mediated by histone deacetylase (HDAC) in a subject in need thereof, the method comprising administering to the subject a pharmaceutically effective amount of a compound of claim 1, wherein the condition is selected from the group consisting of chronic lymphocytic leukaemia, breast cancer, prostate cancer, ovarian cancer, mesothelioma, T-cell lymphoma, cardiac hypertrophy, chronic heart failure, a skin inflammatory condition, a musculoskeletal inflammatory condition, and an inflammatory condition of the gastrointestinal tract.

* * * * *